United States Patent
Kaufmann et al.

(10) Patent No.: US 10,173,019 B2
(45) Date of Patent: Jan. 8, 2019

(54) DRY POWDER DELIVERY DEVICE

(75) Inventors: Nimrod Kaufmann, Modiln (IL); Guy Steuer, Kibbutz Ramot Menashe (IL)

(73) Assignee: Inspiro Medical Ltd., Nes Ziona (IL)

( * ) Notice: Subject to any disclaimer, the term of this patent is extended or adjusted under 35 U.S.C. 154(b) by 968 days.

(21) Appl. No.: 13/519,168

(22) PCT Filed: Dec. 26, 2010

(86) PCT No.: PCT/IB2010/056074
§ 371 (c)(1),
(2), (4) Date: Jun. 26, 2012

(87) PCT Pub. No.: WO2011/077414
PCT Pub. Date: Jun. 30, 2011

(65) Prior Publication Data
US 2012/0291781 A1 Nov. 22, 2012

Related U.S. Application Data

(60) Provisional application No. 61/290,197, filed on Dec. 26, 2009, provisional application No. 61/375,828, filed on Aug. 21, 2010.

(51) Int. Cl.
*A61M 15/00* (2006.01)
*A61M 11/02* (2006.01)
(Continued)

(52) U.S. Cl.
CPC ...... *A61M 15/0028* (2013.01); *A61M 11/001* (2014.02); *A61M 11/02* (2013.01);
(Continued)

(58) Field of Classification Search
CPC ............ A61M 15/0028; A61M 15/003; A61M 15/0003; A61M 15/0035; A61M 11/02; A61M 15/0091
See application file for complete search history.

(56) References Cited

U.S. PATENT DOCUMENTS 5,404,871 A * 4/1995 Goodman et al. ....... 128/200.14
6,739,332 B1 * 5/2004 Higenbottam et al. .. 128/200.13
(Continued)

FOREIGN PATENT DOCUMENTS

WO    WO 02/05879    1/2002
WO    WO 2011/077414    6/2011

OTHER PUBLICATIONS

International Preliminary Report on Patentability dated Jul. 5, 2012 From the International Bureau of WIPO Re. Application No. PCT/IB2010/056074.
(Continued)

*Primary Examiner* — Timothy Stanis

(57) ABSTRACT

A method of flowing a medicament containing powder using gas, including, providing a volume of a gas according to one or more release conditions; directing flow of said gas through or adjacent a powder including a medicament; and releasing a therapeutically effective amount of said powder using said gas. Optionally, the releasing comprises releasing according to breath considerations. Optionally or alternatively, the releasing comprises releasing according to time considerations. In an exemplary embodiment of the invention, the powder is held in a capsule that has apertures formed therein.

62 Claims, 24 Drawing Sheets

(51) Int. Cl.
  *A61M 11/06* (2006.01)
  *A61M 16/20* (2006.01)
  *A61M 11/00* (2006.01)
  *A61M 16/06* (2006.01)
  *A61M 16/14* (2006.01)
  *A61M 16/00* (2006.01)

(52) U.S. Cl.
  CPC .......... *A61M 11/06* (2013.01); *A61M 15/001* (2014.02); *A61M 15/0003* (2014.02); *A61M 15/003* (2014.02); *A61M 15/008* (2014.02); *A61M 15/0016* (2014.02); *A61M 15/0018* (2014.02); *A61M 15/0021* (2014.02); *A61M 15/0035* (2014.02); *A61M 15/0038* (2014.02); *A61M 16/0063* (2014.02); *A61M 16/202* (2014.02); *A61M 16/204* (2014.02); *A61M 11/005* (2013.01); *A61M 15/0045* (2013.01); *A61M 15/0081* (2014.02); *A61M 15/0085* (2013.01); *A61M 16/06* (2013.01); *A61M 16/0666* (2013.01); *A61M 16/14* (2013.01); *A61M 2016/0021* (2013.01); *A61M 2016/0033* (2013.01); *A61M 2202/025* (2013.01); *A61M 2202/0208* (2013.01); *A61M 2202/064* (2013.01); *A61M 2205/07* (2013.01); *A61M 2205/071* (2013.01); *A61M 2205/27* (2013.01); *A61M 2205/276* (2013.01); *A61M 2205/3331* (2013.01); *A61M 2205/3355* (2013.01); *A61M 2205/3553* (2013.01); *A61M 2205/3561* (2013.01); *A61M 2205/3584* (2013.01); *A61M 2205/3592* (2013.01); *A61M 2205/50* (2013.01); *A61M 2205/502* (2013.01); *A61M 2205/52* (2013.01); *A61M 2205/581* (2013.01); *A61M 2205/583* (2013.01); *A61M 2205/6018* (2013.01); *A61M 2205/6054* (2013.01); *A61M 2205/6072* (2013.01); *A61M 2205/8206* (2013.01); *A61M 2205/8237* (2013.01); *A61M 2206/16* (2013.01); *A61M 2209/06* (2013.01); *A61M 2230/201* (2013.01); *A61M 2230/30* (2013.01)

(56) References Cited

U.S. PATENT DOCUMENTS

| | | | |
|---|---|---|---|
| 2001/0029948 | A1 | 10/2001 | Ingle et al. |
| 2003/0116157 | A1* | 6/2003 | Braithwaite et al. .... 128/203.15 |
| 2003/0205229 | A1* | 11/2003 | Crockford ............. A61M 11/06 128/204.23 |
| 2004/0159322 | A1* | 8/2004 | Kladders et al. ........ 128/203.15 |
| 2005/0087189 | A1 | 4/2005 | Crockford et al. |
| 2005/0205087 | A1* | 9/2005 | Kablik et al. ............ 128/200.23 |
| 2005/0263151 | A1 | 12/2005 | Hochrainer et al. |
| 2007/0272763 | A1 | 11/2007 | Dunne et al. |
| 2008/0035143 | A1 | 2/2008 | Sievers et al. |
| 2008/0210242 | A1* | 9/2008 | Burk et al. ............... 128/206.21 |
| 2008/0299049 | A1* | 12/2008 | Stangl ............................. 424/45 |
| 2009/0139517 | A1* | 6/2009 | Wachtel ............ A61M 15/0028 128/200.23 |
| 2009/0293873 | A1* | 12/2009 | Djupesland et al. .... 128/203.15 |

OTHER PUBLICATIONS

Communication Pursuant to Article 94(3) EPC dated May 19, 2015 From the European Patent Office Re. Application No. 10813136.8.
Communication Relating to the Results of the Partial International Search dated May 30, 2011 From the International Searching Authority Re. Application No. PCT/IB2010/056074.
International Search Report and the Written Opinion dated Jul. 26, 2011 From the International Searching Authority Re. Application No. PCT/IB2010/056074.
Communication Pursuant to Article 94(3) EPC dated Feb. 1, 2016 From the European Patent Office Re. Application No. 10813136.8.
Communication Pursuant to Article 94(3) EPC dated Nov. 25, 2016 From the European Patent Office Re. Application No. 10813136.8. (5 Pages).

* cited by examiner

| pulse No. | Weight | drug Weight |
|---|---|---|
| 0 | 0.0715 | 0.0245 |
| 1 | 0.0707 | 0.0237 |
| 2 | 0.0672 | 0.0202 |
| 3 | 0.0633 | 0.0163 |
| 4 | 0.0592 | 0.0122 |
| 5 | 0.0583 | 0.0113 |
| 6 | 0.0579 | 0.0109 |
| 7 | 0.0553 | 0.0083 |
| 8 | 0.0527 | 0.0057 |
| 9 | 0.052 | 0.005 |
| 10 | 0.0503 | 0.0033 |
| 11 | 0.0497 | 0.0027 |
| 12 | 0.0491 | 0.0021 |

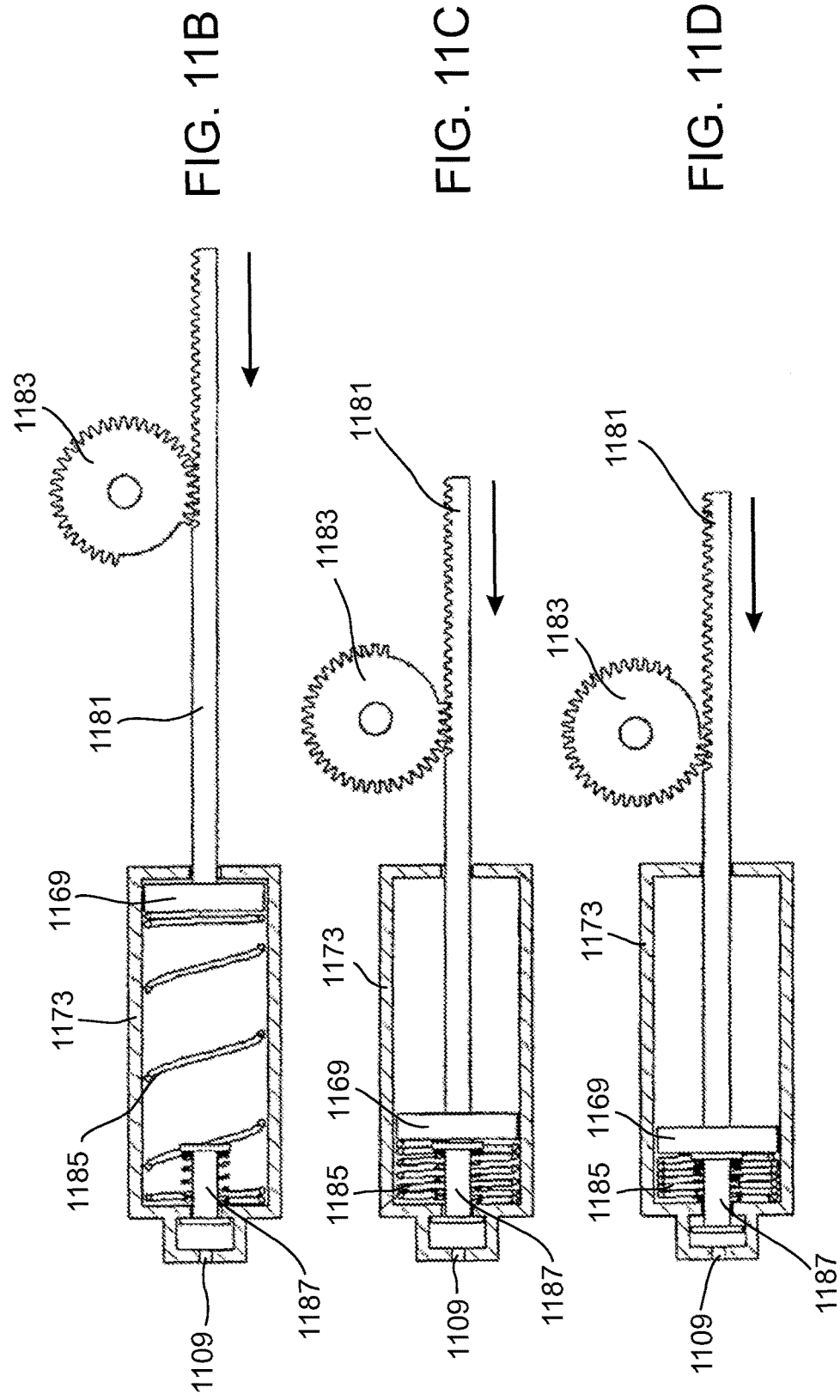

DRY POWDER DELIVERY DEVICE

RELATED APPLICATION/S

This application is a National Phase of PCT Patent Application No. PCT/IB2010/056074 having international filing date of Dec. 26, 2010, which claims the benefit of priority of U.S. Provisional Patent Application Nos. 61/290,197 filed on Dec. 26, 2009 and 61/375,828 filed on Aug. 21, 2010. The contents of the above applications are all incorporated herein by reference.

FIELD AND BACKGROUND OF THE INVENTION

The present invention, in some embodiments thereof, relates to a dry powder delivery device and, more particularly, but not exclusively, to an apparatus and method for controlled delivery of dry powder.

In US patent application 2004/0089299, Bonney et al disclose: "An inhaler for delivery of a dry powder medicament is disclosed that includes a breath sensor for sensing the breath of a patient, a reservoir for the dry powder, a meter for metering an amount of dry powder from the reservoir, and electro-mechanical coupling means for actuating said meter, wherein said coupling means is directly or indirectly responsive to said breath sensor."

In U.S. Pat. No. 6,012,454, Hodson et al disclose: "A dry powder inhaler comprises a housing that has a portion that receives a dose of powdered medicament, a patient port that is placed in fluid communication with a patient; an inhalation passageway in communication with the patient port, a deagglomerator that deagglomerates or assists in aerosolization of the dose of powdered medicament; an electric powered device that drives the deagglomerator; a patient-independent energy output source that drives the electric powered device, a detector that detects inspiratory flow through the inhalation passageway; and a controller for actuating the deagglomerator in response to detection of the inspiratory flow by the detector."

Additional background art includes:
U.S. Pat. Nos. 7,819,116
7,520,278
7,458,373
7,322,355
7,117,867
United States patent application 20090095294
United States patent application 20050056276
United States patent application 20040079368
United States patent application 20030168057

SUMMARY OF THE INVENTION

An aspect of some embodiments of the invention relates to a device for controlled delivering of dry powder. Optionally, the release schedule is according to breath and/or time considerations. Optionally or alternatively, the release is according to one or more release conditions. Optionally or alternatively, the release occurs within a time window, optionally for a significant duration thereof and/or as bursts therein. Optionally or alternatively, the amount released is according to feedback.

There is provided in accordance with an exemplary embodiment of the invention, a method of flowing a medicament containing powder using gas, comprising:

providing a volume of a gas according to one or more release conditions;

directing flow of said gas through or adjacent a powder including a medicament;

releasing a therapeutically effective amount of said powder using said gas.

In an exemplary embodiment of the invention, said releasing comprises releasing according to breath considerations. Optionally or alternatively, said releasing comprises releasing according to time considerations.

In an exemplary embodiment of the invention, said breath considerations comprises an inspiratory flow rate. Optionally or alternatively, said breath considerations comprises an inspiratory flow volume. Optionally or alternatively, said breath considerations comprises a prolonged expiratory phase.

In an exemplary embodiment of the invention, said time considerations comprises a time of day.

In an exemplary embodiment of the invention, said releasing an amount comprises releasing two or more amounts as part of a release logic. Optionally, said powder comprises one powder source. Optionally or alternatively, said two or more amounts are different. Alternatively, said two or more amounts are equal.

In an exemplary embodiment of the invention, said first amount is released during a morning and said second amount is released during an afternoon.

In an exemplary embodiment of the invention, said release condition comprises an inspiratory flow rate higher than a threshold.

In an exemplary embodiment of the invention, said release condition comprises an external reference.

In an exemplary embodiment of the invention, providing comprises providing by dynamically adjusting said volume.

In an exemplary embodiment of the invention, said providing comprises providing by dynamically adjusting a pressure of said gas.

In an exemplary embodiment of the invention, said two or more amounts are dynamically adjusted according to a feedback. Optionally, said dynamically adjusted comprises dynamically adjusting in real time. Optionally or alternatively, said dynamically adjusted comprises dynamically adjusting per breath.

In an exemplary embodiment of the invention, said releasing comprises releasing in a burst, wherein said burst is less than 0.2 seconds in length. Optionally or alternatively, said releasing comprises releasing continuously, wherein said continuously is between 0.5 seconds and 5 seconds in length.

In an exemplary embodiment of the invention, said release condition comprises a delay from the start of an inhalation phase. Optionally, said delay is less than 1.5 seconds.

In an exemplary embodiment of the invention, said release condition comprises a time or a volume before an inert part. Optionally, said inert part ranges from 25% to 75% of an inspiratory volume.

In an exemplary embodiment of the invention, said releasing comprises inhaling as part of a medical therapy.

In an exemplary embodiment of the invention, said releasing comprises blowing into a body cavity.

Optionally, the method further comprises:
providing said powder in a capsule; and
opening said capsule and wherein said directing flow comprises directing through said opening.

In an exemplary embodiment of the invention, said flow deagglomerates said powder. Optionally or alternatively, said flow aerosolizes said powder.

In an exemplary embodiment of the invention, said gas is compressed before a second of said burst There is provided in accordance with an exemplary embodiment of the invention, a dry powder delivery apparatus for delivery of a medicament, comprising:
 a source of a gas;
 a dry powder including a medicament; and
 a staging chamber configured to allow one or more bursts of said gas through or adjacent said powder, thereby releasing a therapeutically effective amount of said powder. Optionally, said gas is a volume of a gas.

In an exemplary embodiment of the invention, the apparatus comprises a compressor.

In an exemplary embodiment of the invention, the apparatus comprises a piston to compress said gas in a cylinder. Optionally or alternatively, the apparatus comprises a tank to store said gas. Optionally or alternatively, the apparatus comprises a handpump to compress said gas.

In an exemplary embodiment of the invention, the apparatus comprises a capsule comprising said powder, wherein said capsule is positioned in said staging chamber. Optionally or alternatively, the apparatus comprises a magazine of capsules comprising said powder. Optionally or alternatively, the apparatus comprises a piercing mechanism to pierce one or more holes in said capsule.

In an exemplary embodiment of the invention, the apparatus comprises a controller configured to control the release of said gas through said chamber. Optionally, said controller is configured to control the release of said powder according to a treatment protocol. Optionally or alternatively, said controller is configured to dynamically control the release of said powder according to a feedback.

In an exemplary embodiment of the invention, the apparatus comprises a facemask, said facemask in fluid communication with said staging chamber.

In an exemplary embodiment of the invention, the apparatus comprises a safety mechanism to restrict access to said powder. Optionally, said safety mechanism prevents access to said powder. Optionally or alternatively, said safety mechanism disposes of said powder.

In an exemplary embodiment of the invention, the apparatus comprises two or more separately stored types of a dry powder.

In an exemplary embodiment of the invention, said apparatus is self powered.

There is provided in accordance with an exemplary embodiment of the invention, a method of delivering dry powder comprising:

providing a first amount of a dry powder in a capsule;

forming one or more apertures in said capsule; and controlling the release of a second amount of said powder from said capsule, wherein said second amount is less than said first amount. Optionally, said second amount is released from the same capsule as said first amount.

There is provided in accordance with an exemplary embodiment of the invention, a method of providing a medicament containing powder comprising:

releasing a therapeutically effective first amount of a dry powder during a breathing cycle; and releasing a therapeutically effective second amount of a dry powder during said breathing cycle, wherein said first and second amounts are separated by a period of time. Optionally, said releasing comprises releasing by flowing a gas through said powder.

There is provided in accordance with an exemplary embodiment of the invention, a dry powder delivery kit for delivery of a medicament, comprising:

a container for positioning one or more capsules comprising a dry powder including a medicament in said apparatus; and a battery for providing power to said apparatus. Optionally, the apparatus comprises a dry powder delivery apparatus for delivery of a medicament. Optionally or alternatively, the apparatus comprises a mouth adapter, said mouth adapter provides a fluid communication between said apparatus and a mouth. Optionally or alternatively, the apparatus comprises a nasal adapter, said nasal adapter provides a fluid communication between said apparatus and a nostril.

There is provided in accordance with an exemplary embodiment of the invention, a method of comparing breathing patterns comprising:

estimating the breathing pattern for release of a dry powder including a medicament; comparing said estimated pattern to an actual breathing pattern during said release; and providing feedback to improve said breathing pattern. Optionally, said comparing comprises comparing in real time.

Unless otherwise defined, all technical and/or scientific terms used herein have the same meaning as commonly understood by one of ordinary skill in the art to which the invention pertains. Although methods and materials similar or equivalent to those to described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Figure 8A:
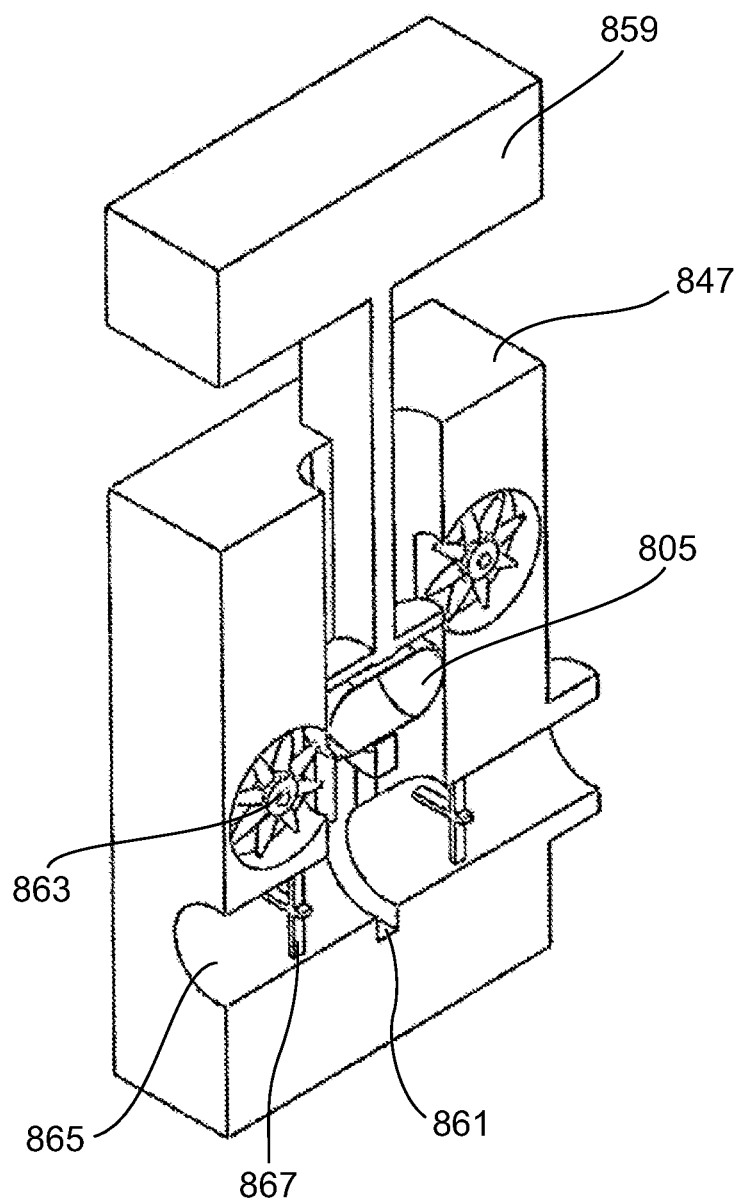
Figure 8B:
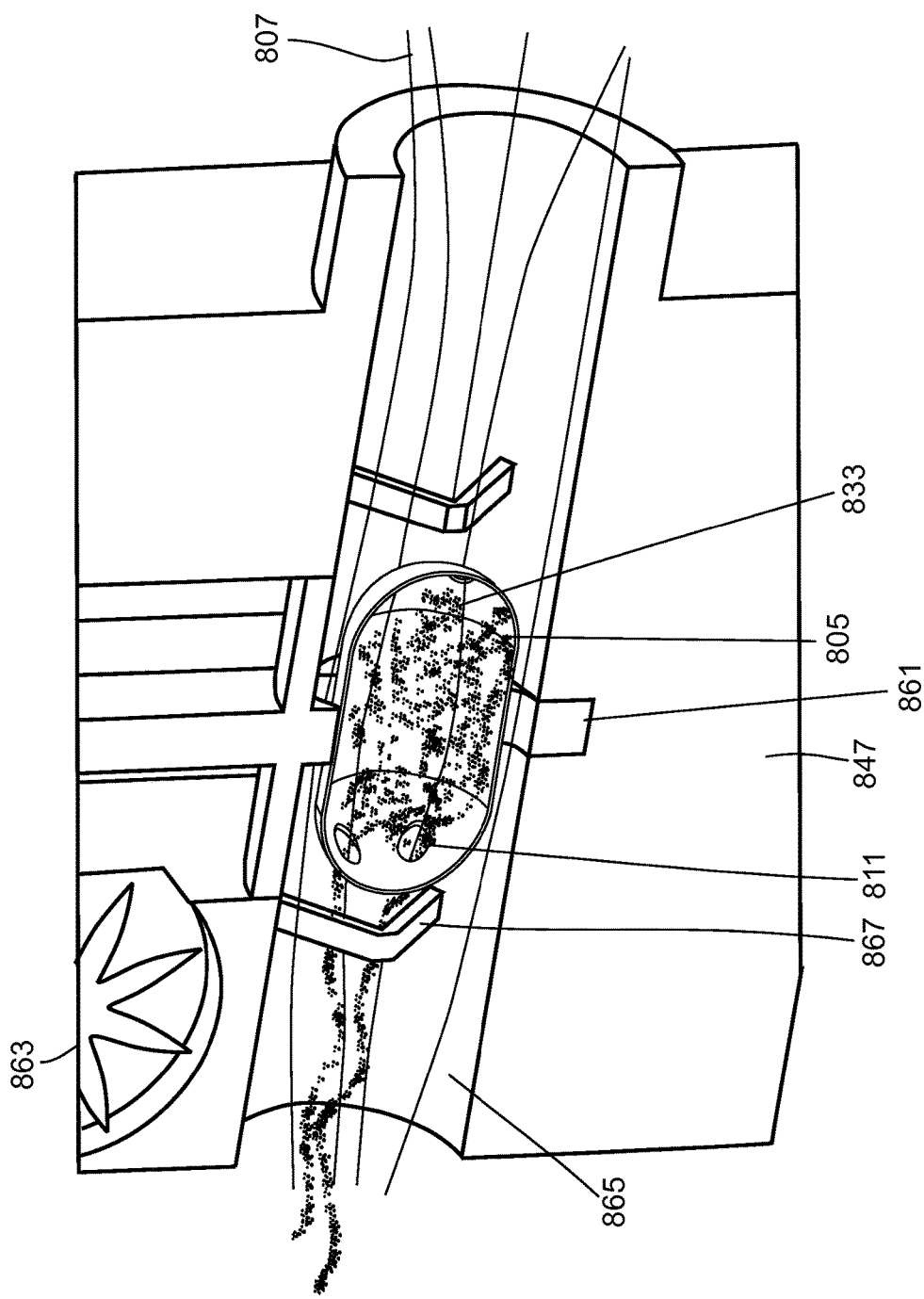
Figure 9:
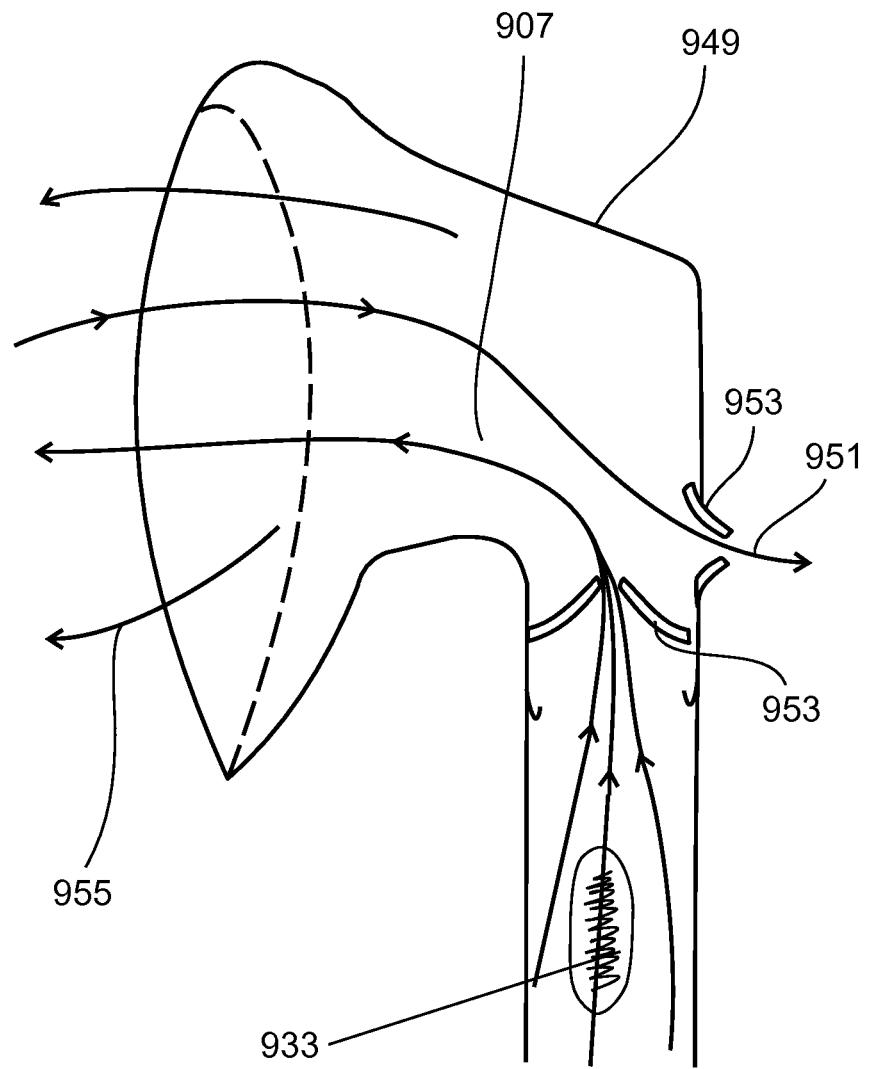
Figure 10:
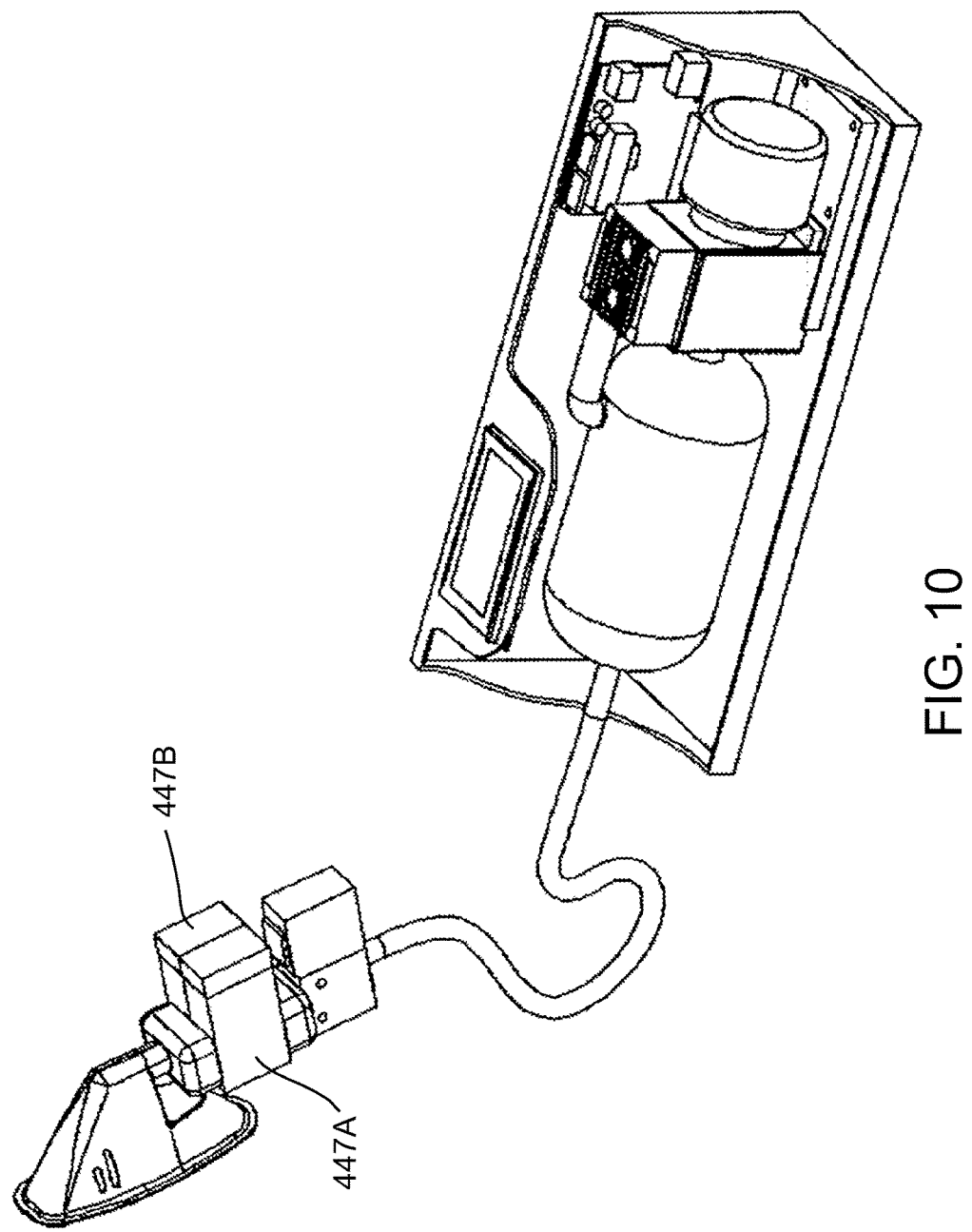
Figure 11A:
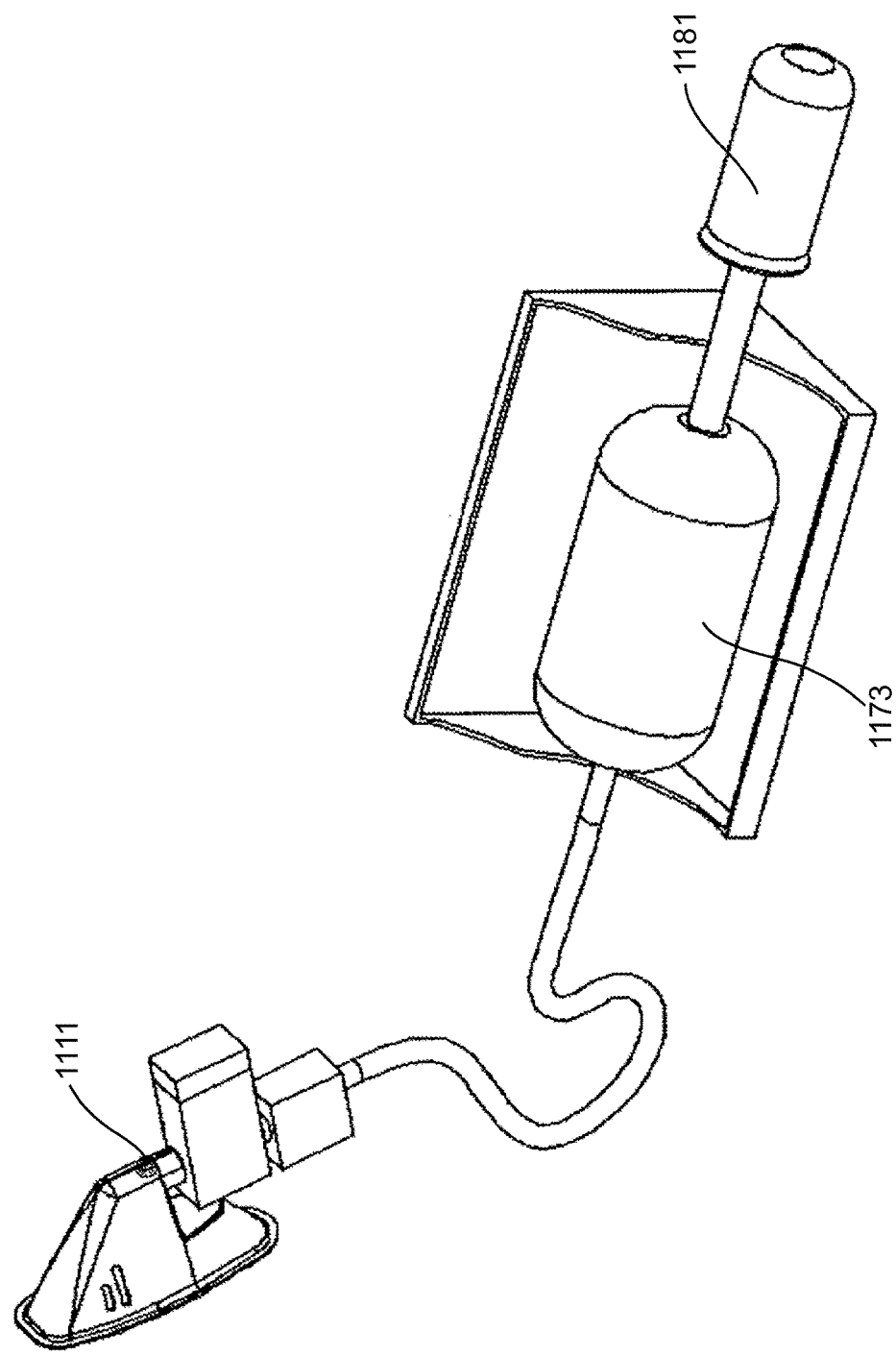
Figure 12:
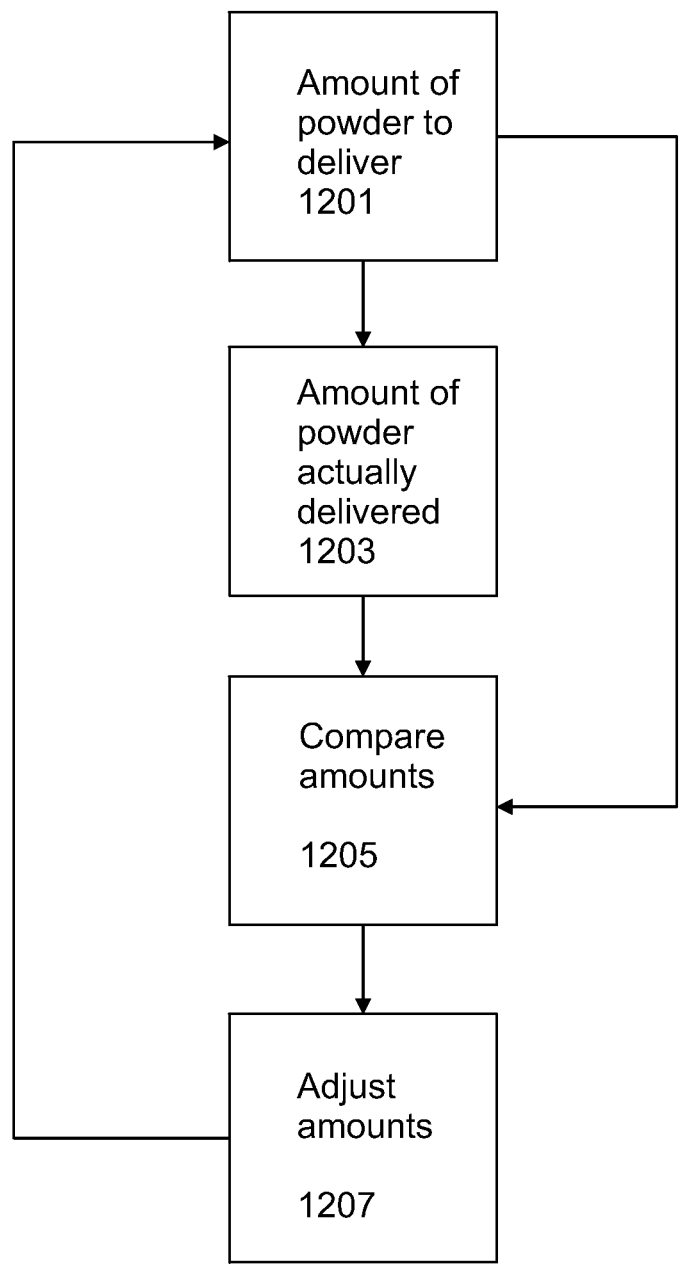
Figure 13:
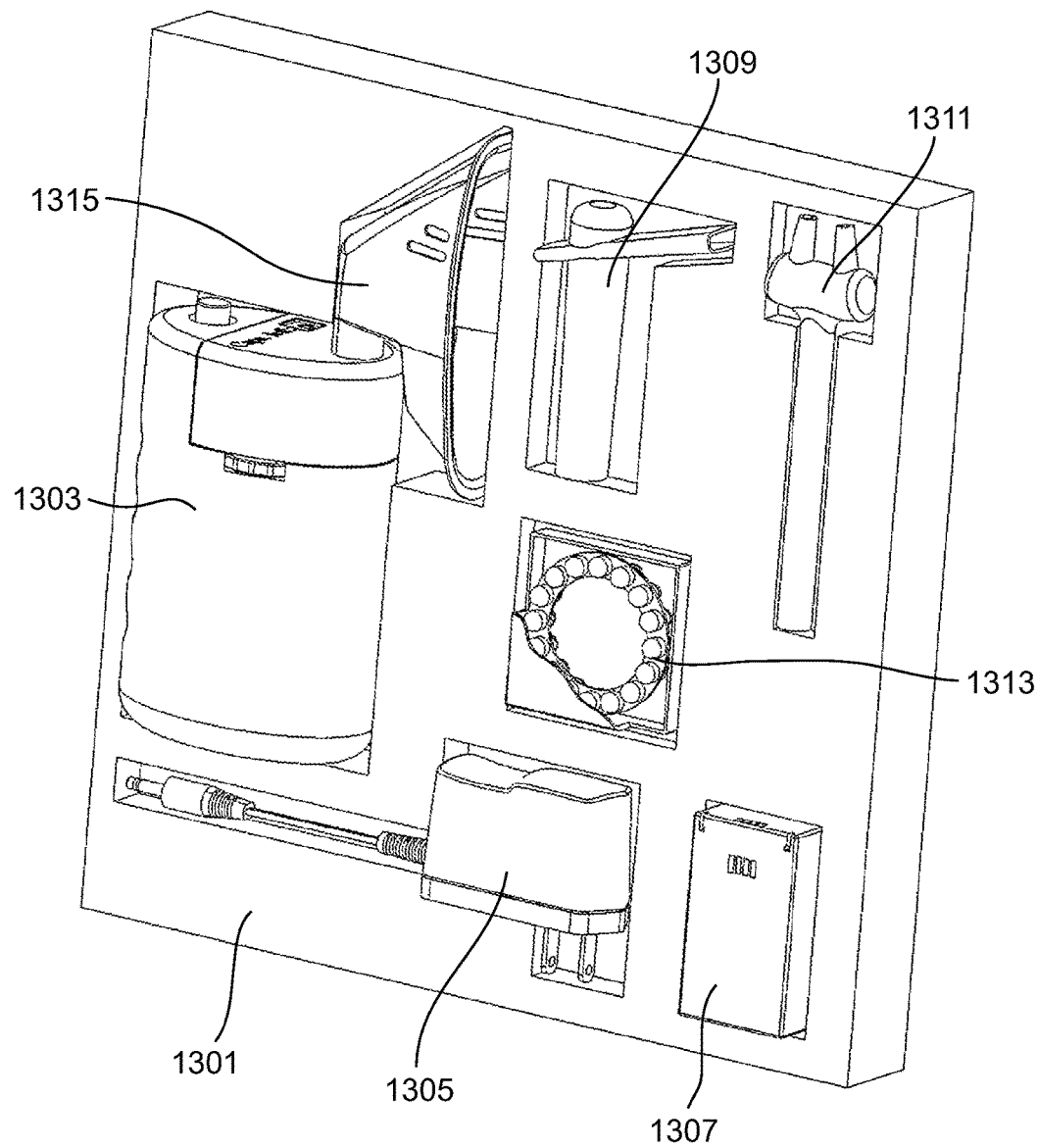
Figure 14:
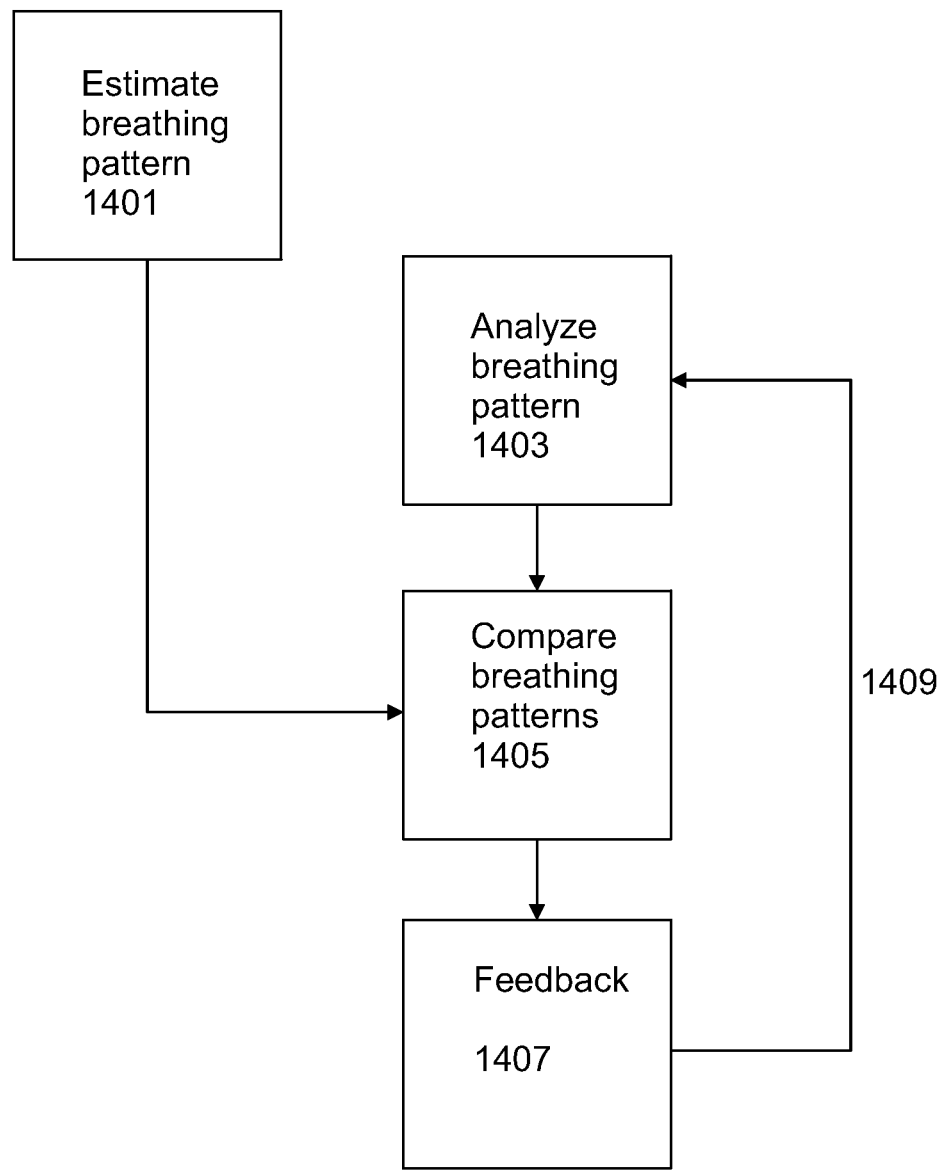

FIG. 6A-D illustrate alternative designs of the source of compressed gas, used in accordance with an exemplary embodiment of the invention;

FIG. 7A-F illustrate the ability of the inhaler to control the delivery of dry powder, in accordance with an exemplary embodiment of the invention;

FIGS. 8A and 8B illustrate an exemplary design of a loading chamber, in accordance with an exemplary embodiment of the invention;

FIG. 9 illustrates an exemplary design of a mask, in accordance with an exemplary embodiment of the invention;

FIG. 10 illustrates an embodiment of two loading chambers, in accordance with an exemplary embodiment of the invention;

FIG. 11A-D illustrate an all mechanical inhaler design, in accordance with an exemplary embodiment of the invention;

FIG. 12 is a method of adjusting the amount of powder to be delivered based on feedback about the amount actually delivered, in accordance with an exemplary embodiment of the invention;

FIG. 13 is an illustration of an exemplary kit, in accordance with an exemplary embodiment of the invention; and FIG. 14 is a method of comparing the inhalation pattern of the patient to the inhalation pattern that will potentially result in an improved delivery of powder.

DESCRIPTION OF SPECIFIC EMBODIMENTS OF THE INVENTION

The present invention, in some embodiments thereof, relates to a dry powder delivery device and, more particularly, but not exclusively, to an apparatus and method for controlled delivery of dry powder.

An aspect of some embodiments of the invention relates to the controlled delivery and/or release of a dry powder using a gas. Optionally or alternatively, the release schedule is determined by breath and/or time considerations. Optionally or alternatively, the release schedule is determined by feedback.

In an exemplary embodiment of the invention, release of dry powder occurs as a short burst. Optionally or alternatively, the dry powder is released as a succession of short bursts. Optionally or alternatively, the dry powder is released continuously over a period of time.

In an exemplary embodiment of the invention, dry powder is a drug used as part of medical therapy.

In an exemplary embodiment of the invention, the release of two or more types of powder is controlled. Optionally, two or more powder types are simultaneously released. Optionally or alternatively, release of each powder type occurs at different times.

In an exemplary embodiment of the invention, after release, dry powder is transported to target tissues by an inspiratory flow. Alternatively, dry powder is blown to target tissue (eg. lungs, cavity such as nasal cavity) using gas.

In an exemplary embodiment of the invention, dry powder release occurs according to one or more release conditions. Optionally, the release condition is associated with the inspiratory phase. Optionally or alternatively, the release condition is an inspiratory flow rate higher than a threshold. Optionally or alternatively, the release condition is secondary to the inspiratory phase In an exemplary embodiment of the invention, the amount of dry powder released is controlled. The amount of dry powder released is within a precision range. Optionally, successive amounts released are from the same source of powder. Optionally or alternatively, the amount of successive releases of powder is approximately equal. Optionally or alternatively, the amount of successive releases of powder varies according to breath and/or time considerations.

In an exemplary embodiment of the invention, the amount of dry powder to release is controlled according to feedback. Optionally, feedback is based on the amount of dry powder previously delivered. Optionally or alternatively, feedback is based on user input.

In an exemplary embodiment of the invention, the efficiency of delivery is estimated.

In an exemplary embodiment of the invention, the effectiveness of breathing is estimated. Optionally, feedback is provided to the patient and/or is stored on memory of inhaler 101 for subsequent retrieval such as by a physician.

In an exemplary embodiment of the invention, dry powder is released within a time or breathing cycle range. Optionally, the start of the range is a delay from inhalation. Optionally or alternatively, the end of the range is the start of an inert phase.

An aspect of some embodiments of the invention relates to a dry powder delivery device comprising a volume of a gas, a dry powder and a staging chamber. Dry powder is released from the staging chamber by a burst of the gas. Optionally, a capsule comprises the dry powder. Optionally or alternatively, the capsule is pierced by a piercing mechanism.

An aspect of some embodiments of the invention relates to the controlled release of an amount of powder from a capsule. The capsule is pierced at one or more locations. Optionally, two or more amounts of powder from the capsule are released during one or more breaths.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The to invention is capable of other embodiments or of being practiced or carried out in various ways.

Referring now to the drawings, FIG. 1*a* is a block diagram of a dry powder inhaler 101, in accordance with an exemplary embodiment of the invention. Dry powder inhaler 101 provides a controlled release of a dry powder 131. A fluidizing mechanism 103 uses a source of compressed gas 107 to release powder 131.

In an exemplary embodiment of the invention, fluidizing mechanism 103 regulates compressed gas 107 to release powder 131. Optionally, a volume of gas 107 at a preset pressure releases an amount of powder 131, for example, as will be described in more detail below. Optionally or alternatively, powder 131 is aerosolized in gas 107. Optionally or alternatively, powder 131 is deagglomerated using gas 107. Further details about the design and function of mechanism 103 will be provided below.

In some embodiments of the invention, the amount of powder 131 released is determined by flow of gas 107. In other embodiments, the amount of powder 131 released is controlled by a downstream valve that is timed to shut, such as according to a desired delivery amount, and/or according to a measurement (eg. opacity) of the flowing powder.

In an exemplary embodiment of the invention, gas 107 is room air. Alternatively, gas 107 is for example, one or more of, oxygen, oxygen plus room air, helium plus oxygen (Heliox), and/or anesthetic.

In an exemplary embodiment of the invention, gas 107 compression occurs automatically by a compression mechanism inside inhaler 101, for example, as will be described below. Alternatively, compression of air 107 is manual, without electrical power, for example, as will be described below. Alternatively, the source of compressed air 107 is provided by an external source, for example, a gas tank.

In an exemplary embodiment of the invention, the supply of gas 107 is sufficient to deliver and/or release powder 131, for example, for one or more of, one breath, one capsule, set of capsules, one treatment, or other smaller, intermediate or larger measurements. Release of powder can refer for example to the amount that inhaler 101 releases from the total supply, such as from the capsule. Delivery of powder can refer for example, to the amount of powder that was actually inspired, such as the fraction of the released powder, such as 70%, 80%, 90%, 100% or other smaller, intermediate or larger to fractions of released powder that was released.

In an exemplary embodiment of the invention, the total volume of gas 107 used to release powder 131 during one breath ranges from 0.1 ml to 100 ml, for example, from 1 ml to 50 ml, from 10 ml to 30 ml, or other smaller, intermediate or larger volume ranges. Optionally, the volume of gas 107 used to release powder 131 during one pulse ranges from 0.1 to 10 ml, for example, 1 ml to 5 ml, 2 ml to 4 ml, or other smaller, intermediate or larger volume ranges. Optionally or alternatively, gas 107 can be used to supply oxygen to a patient, for example by being attached to a mechanical ventilation machine, in which case, volume of gas 107 per breath can range from 0.1 ml to 200 ml, for example, 100 ml to 200 ml, or other smaller, intermediate or larger volume ranges.

In an exemplary embodiment of the invention, the pressure of gas 107 used to release powder 131 ranges from 0.5 bar to 10 bar, for example, 0.5 bar to 6.7 bar, for example, 4.5 bar to 6.7 bar, or other smaller, intermediate or larger pressures.

In some embodiments of the invention, the inspiratory flow is used in conjunction with gas 107 to release powder 131. Alternatively, the inspiratory flow alone is used to release powder 131.

In an exemplary embodiment of the invention, powder 131 includes a medicament. Optionally, powder 131 includes a carrier (eg. inert substance), such as lactose and/or glucose, for example, to increase the amount of powder in order to reduce error rates during release (eg. it is easier to control the release of 1 mg from 10 mg, as opposed to 1 mcg from 10 mcg). The amount of carrier, such as relative to the amount of powder 131 can be set to match the flow characteristics of gas in several ways, for example, by calibration. The percent of carrier to drug can vary, for example, from 0.001% to 100%, from 0.01~0.1%, or other smaller, intermediate or larger ranges. For example, approximately 0.05% for a drug such as budesonide. For example, approximately 100% for salt (sodium chloride) powder.

In an exemplary embodiment of the invention, one or more powder 131 delivery modes are available. Optionally, gas 107 releases powder 131 such that powder 131 is suspended, for example in a cloud like formation. A potential advantage is that powder 131 enters the lungs of the patient through the inspiratory efforts of the patient. Optionally or alternatively, gas 107 pushes released powder 131 into the lungs of the patient. A potential advantage of pushing and/or blowing powder 131 into the patient, such as into the lungs, nasal cavity and/or mouth of the patient is delivery of powder to patients that are unable to generate an adequate inspiratory flow. A potential advantage of not releasing powder during inhalation, for example, during the inert part and/or during exhalation, is to target powder 131 delivery to tissues such as the nasal cavity, mouth and/or upper airways.

A potential advantage of the controlled release of powder 131, in accordance with some embodiments of the invention, is that a patient does not need to be provided with any special breathing instructions, since the release, deagglomeration and/or aerosolization of powder 131 is all provided by inhaler 101. The patient can breathe normally, and/or in a pattern that is comfortable, as the inhaler 101 adjusts to the breathing pattern of the patient to release powder 131 accordingly. Patients that may especially benefit from using inhaler 101 include one or more of, those that may have difficulty in coordination, following instructions and/or breathing deeply, such as children, the elderly, the disabled, those suffering from certain diseases (eg. weakness of chest wall muscles). In some embodiments of the invention, patients are provided with special breathing instructions.

In an exemplary embodiment of the invention, powder 131 includes a medicament. Optionally, an amount of powder that is therapeutically effective is released for inhalation as part of medical therapy. Optionally or alternatively, powder 131 is used for testing, for example, testing the functionality of inhaler 101, and/or testing a patient for an allergic reaction.

Controlled Powder Release

FIG. **2*a* is a method of controlling the release of an amount of dry powder 131, in accordance with an exemplary embodiment of the invention. One or more release conditions are detected, for example, as will be described below. An amount of dry powder 131 is released by controlling the volume and/or the pressure of gas 107**.

At 202, one or more release conditions that trigger the release of powder 131 are present. Optionally, the release condition is automatically monitored and/or detected, for example, as will be described below. Alternatively, the release condition is manually set, for example using a button and/or switch.

In an exemplary embodiment of the invention, the release condition is associated with the inspiratory phase. Optionally, the release condition is the instantaneous inspiratory flow rate above a threshold, for example, greater than 30 liters/min, 20 liters/min, 10 liters/min, or other smaller, larger or intermediate values of inspiratory flow rates. Alternatively, dry powder 131 is released at a range, for example, the instantaneous inspiratory flow rate between 20 liters/min and 65 liters/min, inspiratory flow rate between 30 liters/min and 45 liters/min Optionally or alternatively, dry powder is released at the point of maximal inspiratory flow rate during the current inspiratory phase, for example, the point at which the flow rate begins to decrease.

Examples of one or more other release conditions associated with the inspiratory phase include, carbon dioxide content, oxygen content, moisture content, pressure. One or more sensors can be located for example in one or more locations such as, the face mask, the tube, the outlet port.

In some embodiments of the invention, the release condition is a blood glucose level higher and/or lower than a threshold, for example, for releasing inhaled insulin powder 131, as will be described in more detail with reference to FIG. 7E.

In some embodiments of the invention, the release condition is related to a secondary effect and/or secondary measure, for example, a side effect of treatment. For example, before inhaler 101 delivers morphine to a patient such as for pain management, the blood pressure is checked against a threshold. For example, morphine release is prevented if the systolic blood pressure is too low, such as less than 110 mmHg, less than 90 mmHg, less than 80 mmHg or other smaller, intermediate or larger blood pressures. One or more examples of other release conditions include, a time of day for delivering the drug (eg. insulin for diabetes, desmopressin for diabetes insipidus), a heart rate threshold (eg. prevent toxicity due to bronchodilators) such as heart rate greater than 120 beats per minute, 150 beats per minute, 180 beats per minute, or other smaller, intermediate or larger beats per minute.

Another example of treatment by inhalation is antibiotics, such as to treat infection in patients with chronic lung disease (eg. cystic fibrosis). One or more examples of antibiotics include, TIPI (Tobramycin Powder for inhalation), Aztreonam, Ciprofloxacin, and/or Amphtericin.

In some embodiments of the invention, the release condition is associated with the expiratory phase. Optionally, the release occurs during the inspiratory phase following a prolonged exhalation (such as, a normal variation in a child's breathing cycle, in a cry and/or a sigh), for example, in an expiratory phase greater than 66%, 75%, 80%, 90% of the breathing cycle (eg. inspiration plus expiration), or other smaller, intermediate or larger percentages. Another example of a prolonged expiratory phase is an expiratory volume greater than the previous inspiratory volume. A potential advantage of a release during the inspiratory phase following a prolonged expiratory phase is an expected increase in the inspiratory flow rate and/or volume that may result in a higher percentage of powder particles deposited at the target tissue.

At 204, a controlled amount of dry powder 131 is released by controlling the volume and/or pressure of gas 107.

Figure 3:
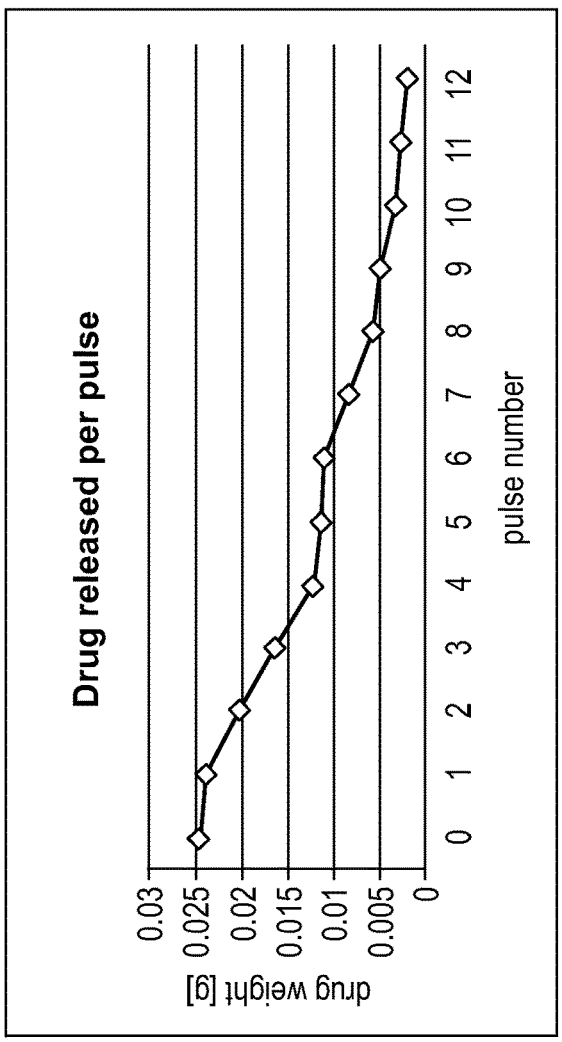
FIG. 3 is a graph of a calibration curve, useful in practicing some embodiments of the invention.

Inventors have discovered that the amount of dry powder 131 released is proportional to the volume and/or pressure of gas 107 used to release powder 131. Inventors have performed calibration experiments for one type of drug (Foradil) using a constant volume (three milliliters) of gas 107 at a constant pressure (two atmospheres). Further details will be provided with reference to FIG. 3. The results of the discovery of the inventors can potentially be used to control the continuous release of powder 131, for example, by controlling the flow (eg. liters per minute) of gas 107 at a set pressure.

In an exemplary embodiment of the invention, the amount of powder 131 released is within a threshold of precision and/or accuracy, for example, +/−25%, +/−10%, +/−1%, or other smaller, intermediate or larger percentages.

In an exemplary embodiment of the invention, powder 131 release occurs in a burst, for example, in less than 0.01 seconds, 0.05 seconds, 0.1 seconds, 0.2 seconds, or other smaller, intermediate or larger time periods. Optionally or alternatively, powder 131 is released two or more times during the same inspiratory phase, such as in two or more bursts and/or release periods. The number of bursts per second can be as fast as 1 per second, 10 per second, 100 per second, or other smaller, intermediate or larger numbers. The weight of powder at each burst can vary, for example, from 100 mcg to 1000 mcg, from 200 mcg to 400 mcg, or other smaller, intermediate or larger weights.

In an exemplary embodiment of the invention, powder 131 release is prolonged, for example occurring during 10%, 30%, 50% of the inspiratory cycle time and/or volume, or other smaller, intermediate and/or larger percentages. Optionally or alternatively, powder 131 is released over a range of time within one breath, for example, from 0.1 seconds to 3 seconds, from 0.5 to 2 seconds from 0.5 to 1 second, or other smaller, intermediate or larger ranges of time.

Powder Release Options

In an exemplary embodiment of the invention, powder 131 releases are controlled over a number of breaths, for example, 3, 5, 10, 50, 100, or other smaller, intermediate or larger number of breaths. Optionally, the amount of powder 131 per breath is approximately equal. Alternatively, the amount of powder 131 released varies by breath. For example, the drug dosage during the first 10 breaths can be double the dosage during the last 10 breaths. For example, the drug dosage may only be released in one out of every 5, 10, 50, 100 breaths or other smaller, intermediate or larger numbers of breaths. For example, the drug dosage per breath can be adjusted according to feedback, as will be described herein.

In an exemplary embodiment of the invention, powder 131 releases are time limited as well as and/or instead of the number of breaths, for example, being released during the first breath after 20 seconds, being released with a separation of 5 seconds, 10 seconds, 60 seconds between releases, or other smaller, intermediate or larger seconds of separation.

In an exemplary embodiment of the invention, powder 131 releases are controlled over a period of time, for example 30 seconds, 1 minute, 5 minutes, 30 minutes, 1 hour, 8 hours, or other smaller, intermediate or larger numbers of seconds, minutes and/or hours. Optionally or alternatively, an amount is released and/or treatment is stretched out over time.

In some embodiments of the invention, inhaler 101 is continuously in fluid communication with the patient, for example, by the patient wearing a mask. Optionally or alternatively, an alert is provided to the patient to signal to wear the mask before the next release of powder 131.

In an exemplary embodiment of the invention, inhaler 101 controls the amount actually released during the next release (eg. when the patient wears the mask), for example, according to preset ranges, programmed protocol and/or feedback. In an exemplary embodiment of the invention, inhaler 101 provides a placebo burst, wherein gas 107 is released without powder, for example, when a user has reached a maximum threshold such as the amount of morphine allowed. Optionally or alternatively, gas 107 is released with carrier but without powder 131, so patient can taste powder. A potential advantage of the placebo burst is to provide the placebo effect to the patient.

In an exemplary embodiment of the invention, the amount of powder 131 to be released per breath over the time period is controllable, for example, as described herein.

A potential advantage of an extended release of powder according to some embodiments of the invention, is reducing the risk of overdose toxicity and/or side effects, for example in susceptible patients, such as children, the elderly, those with allergic drug reactions, those with genetic predisposition for drug toxicity. Many of the drugs used as examples herein are potentially toxic.

A potential advantage of an extended release of powder according to some embodiments of the invention is improved clinical outcomes. For example, for one or more drugs including, mucolytics (eg. Dornase alpha, sodium chloride, Acetylcystein), antiproteases (eg. alpha1 anti trypsin), medications that positively alter alveolar lining fluids moieties (eg. bicarbonate), medications that are enhanced by a previous dose of the same medication (eg. a small dose of a bronchodilator for severe asthma potentially opens up the airways so that one or more of the next doses of the ronchodilator are inhaled more deeply by the patient), and/or drugs with a short half life (eg. for the treatment of pulmonary hypertension).

In an exemplary embodiment of the invention, the release of powder 131 occurs according to a feedback associated with the breathing pattern of the patient, for example, as will be described in the section titled "Adjusting Doses Based on Feedback". Optionally, the dose and/or amount to be released are adjusted according to the feedback, for example, as described herein.

Controlled Release of an Amount of Powder

Figure 2A:
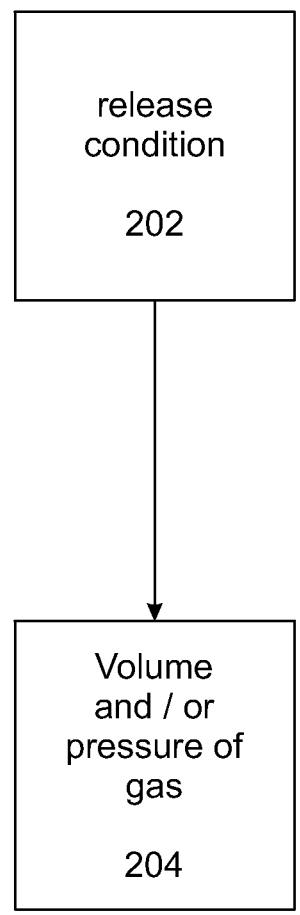
FIG. 2A is a method of controlling the release of an amount of dry powder, in accordance with an exemplary embodiment of the invention.
Figure 2B:
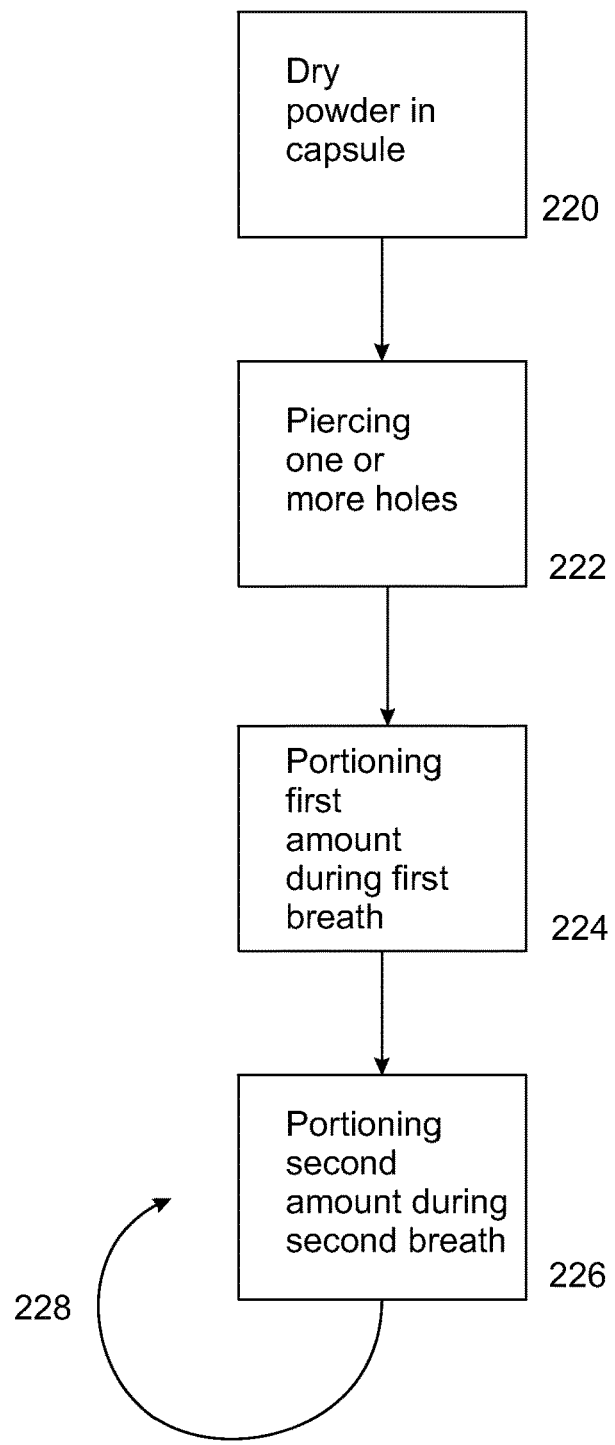
FIG. 2B is a method of using a capsule to release an amount of dry powder over a plurality of inspiratory breaths, in accordance with an exemplary embodiment of the invention.

FIG. 2b is a method of using a capsule to release an amount of dry powder 131 over a plurality of inspiratory breaths, in accordance with an exemplary embodiment of the invention. A capsule comprising dry powder 131 is pierced with one or more apertures and/or holes (as will be described below). Optionally or alternatively, a piece is sliced off the capsule, such as by a knife. Optionally or alternatively, the capsule is pulled apart, such as by a mechanical structure. Optionally or alternatively, one or more preformed apertures are revealed, such as in a covered capsule when the cover is removed. An amount of powder 131, smaller than the total amount in the capsule, is released during a first inspiratory breath, for example, as described herein. From the remaining powder 131 in the capsule, one or more amounts are released during one or more additional inspiratory breaths.

A potential advantage of removing a portion of the total amount of powder 131 from the capsule, is that inhaler 101 can be used by patients that require a smaller dose than one available in a standard capsule, such as infants, children, the elderly. For example, inhaler 101 can release a 250 mg dose from a 500 mg capsule. Alternatively, patients may not inhale an entire dose efficiently due to their physical condition (eg. muscle weakness, lung disease) and/or age (eg. infant with small lung volume), and so would require smaller doses over a number of breaths.

At 220, a capsule 105 comprising dry powder 131 is provided.

In an exemplary embodiment of the invention, capsule 105 is placed inside mechanism 103, in fluid communication with gas 107, as will be described below.

At 222, one or more holes are pierced in capsule 105.

In an exemplary embodiment of the invention, one hole is pierced at each end of the capsule, such that gas 107 can enter a first hole and exit from a second hole. Details of the piercing of capsule 105 along with various alternative embodiments will be provided below.

At 224, a first amount of powder is released during a first inspiratory breath, for example, as described herein. The trigger for release, the time during the inspiratory phase within which to release, and the amount of powder 131 to release are for example, as described herein.

In some embodiments of the invention, an amount of powder is released without gas 107. Optionally, release occurs from one or more holes (eg. on bottom or side) by mechanical impact to capsule, for example, vibration. The amount of powder released by various intensities and/or types of mechanical impact can be calibrated, for example, using a method similar to the one described herein for calibration of an amount released using pressure and/or volume of gas.

In some embodiments of the invention, inhaler 101 does not comprise gas 107. Inspiratory force is used to release powder 131.

At 226, a second amount of powder is released during a second inspiratory breath, for example, as described herein. Alternatively, a second amount of powder is released during the first inspiratory breath as in 224.

At 228, one or more additional amounts of powder 131 are released during one or more subsequent inspiratory breaths as in 226.

In an exemplary embodiment of the invention, a volume of gas 107 is released at the beginning and/or end of treatment to clear any residual powder 131 from inhaler 101, for example from mechanism 103, port 109 and/or any additional air flow components such as tubes. Alternatively, gas 107 is released before and/or after a new drug is delivered.

In an exemplary embodiment of the invention, the releases of powder as in 224, 226 and/or 228 occur as part of a release logic, for example, according to a treatment protocol (as will be described below).

Safety

In an exemplary embodiment of the invention, residual powder 131 remaining after treatment is safely disposed of. In the case of toxic substances, powder 131 can be made indigestible, for example, by mixing in a substance (eg. glue, fluid) to bind and keep powder 131 from being accessed from inside capsule 105. Optionally, capsule 105 comprises a chamber comprising the glue and/or fluid. Optionally or alternatively, an inertizing fluid is provided by inhaler 101. Optionally or alternatively, to dispose of powder 131 in capsule 105, capsule is pushed into a closed container and/or crushed such that it is combined with the glue and/or fluid. The bound powder 131 can then be disposed of in a safe manner. Optionally or alternatively, capsule 105 contain a dosage suitable for a single treatment. During treatment the entire contents of capsule 105 is consumed, so no residual remain.

In an exemplary embodiment of the invention, access to powder 131, such as drugs that are toxic and/or addictive (eg. morphine) is restricted. Inhaler 101 can be equipped for example, with an access code to allow authorized use (eg. physician only) and/or have set safety thresholds that cannot be exceeded (eg. for morphine doses). Optionally or alternatively, access is restricted according to a feedback effect on the patient, for example, if the blood pressure of the patient is decreasing (eg. below 90 mmHg systolic) as a side effect of treatment (eg. to morphine).

Delay and Inert Release Options

Inventors hypothesize that releasing powder 131 within a range of the inspiratory breath will increase the amount of powder 131 that reaches the target tissue inside the lungs, including deep inside the lungs. Inventors hypothesize that the range of release is associated with the anatomy of the patient's airway. The normal anatomy comprises an approximately 90 degree turn from the mouth towards the lungs (eg. junction of the nasopharynx and oropharynx). Inside the lungs of the patient, the normal anatomy comprises corners and/or turns, such as at the point where larger airways branch into smaller airways. Inventors hypothesize that if particles of powder 131 travel within a flow rate range, for example, 10-80, 20-60, 30-50, 35-45 liters/minute or other smaller, intermediate or larger ranges of flow rates, they will flow in the middle of the airway, thereby increasing the amount that reaches the deep parts of the lungs. Potentially, the amount of powder 131 that is deposited outside the lungs, such as at the junction of the nasopharynx and oropharynx, the mask, the mouth, the large airways, the gastrointestinal tract, will be reduced.

Inventors hypothesize that the last part of the air entering the patient during the inspiratory phase fills the space of the large airways and/or pharynx. The last part of the air volume is inert, as powder 131 released during this period may not have a therapeutic effect as it might not reach the deep parts of the lungs. Inventors hypothesize that powder 131 should not be released during the inert part of the inspiratory cycle if the target tissue is for example, the lungs. Alternatively, inventors hypothesize that powder 131 should be released during the inert part if the target tissue is for example the upper respiratory system.

It should be noted that even if one or more of the hypotheses described herein are incorrect, the function of some embodiments of the invention is not precluded. Furthermore, even if the hypothesis is incorrect, there may be other benefits to a controlled release of powder 131 within the range.

A potential advantage of releasing powder 131 within the range of the inspiratory cycle is to reduce oropharyngeal deposition, thereby potentially preventing cardiac mortality, a possible complication in patients that use meter dose inhalers (MDIs) incorrectly.

In an exemplary embodiment of the invention dry powder 131 is released at an approximate point within the inspiratory cycle. Optionally, the point lies in an approximate range within the inspiratory cycle.

In an exemplary embodiment of the invention, release of powder occurs after a delay from the start of inspiration. Optionally or alternatively, the start of inspiration is estimated and/or calculated if the point of the start of inhalation is missed. The delay is set, for example, using one or more of, a look-up table, calculations, manually. Optionally, delay is measured in units of time, for example, for an adult ranging from 1ms to 5.00 seconds, from 1 ms to 1.5 seconds, from 10 ms to 1000 ms, from 20 ms to 500 ms, from 20 ms to 300 ms, from 10 ms to 100 ms, or other smaller, intermediate or larger time ranges. For example, for an infant, ranging from 1 ms to 30 ms, from 10 ms to 20 ms, or other smaller, intermediate or larger time ranges. Alternatively, delay is measured in units of volume of inspired air, for example, for adults, ranging from 1 ml to 400 ml, from 20 ml to 200 ml, from 30 ml to 100 ml, or other smaller, intermediate or larger ranges of volumes. For example, for an infant, from 1 ml to 10 ml, from 2 ml to 5 ml, or other smaller, intermediate or larger ranges of volumes. Alternatively, delay is measured by percent of total inspiratory time and/or volume, for example, from 0.2% to 70%, from 1% to 50%, from 5% to 15%, or other smaller, intermediate or larger percentage ranges.

In an exemplary embodiment of the invention, release of dry powder 131 does not occur during the inert part of the inspiratory phase. Optionally, the inert part is measured in volume and/or time corresponding to the last 25%, 33%, 50%, 70%, of the inspiratory volume, and/or other smaller, intermediate or larger percentages of the inspiratory volume. Alternatively, the inert part is measured by volume, for example 50 ml, 100 ml, 150 ml, 200 ml, or other smaller, intermediate or larger volumes.

In some embodiments of the invention, release of dry powder 131 occurs during the inert part, such as if the powder 131 is meant to act on tissues of the upper respiratory system, for example, as will be described below.

In some embodiments of the invention, the total inspiratory time and/or volume is estimated according to one or more previous inspiratory cycles and/or cycle parameters (eg. volume, flow rate, breathing pattern), for example, the average of the previous two (2), three (3), five (5) cycles, or other smaller, intermediate or larger numbers of cycles. Optionally or alternatively, normal values are used, such as tidal volume, for example for patients with similar profiles, for example, age, weight, disease, disease severity. Optionally or alternatively, values are set according to a drug and/or a powder particle size, for example, as described herein. Optionally or alternatively, values are set manually.

In an exemplary embodiment of the invention, the delay is the first value in the range. In an exemplary embodiment of the invention, the start of the inert part is the second value in the range.

In an exemplary embodiment of the invention, dry powder 131 is released after the delay, before the inert part, and/or once the flow rate threshold has been exceeded. Alternatively, powder 131 is released if the delay has been exceeded, but the threshold has not been met, such as in the case of an infant and/or older patient that cannot generate the required airflow rate within one or more breaths (eg. due to shallow breathing from muscle weakness). Alternatively, release of powder 131 occurs without relation to the delay.

A potential advantage of controlling the release during the range is to control the delivery of powder to target tissues. For example, releasing powder 131 earlier in the inspiratory cycle, for example, during the first 5%, 10%, 15% of the inspiratory volume, or other smaller, intermediate or larger values, may allow maximum deposition in the lungs, potentially useful for treating disorders such as cystic fibrosis and/or asthma. For example, releasing powder 131 during the inert part may allow maximum deposition in non-oxygen exchanging region such as the larynx and/or nose, potentially useful for delivering treatment such as for laryngeal edema, local antifungal treatment, local chemotherapy.

Figure 2C:
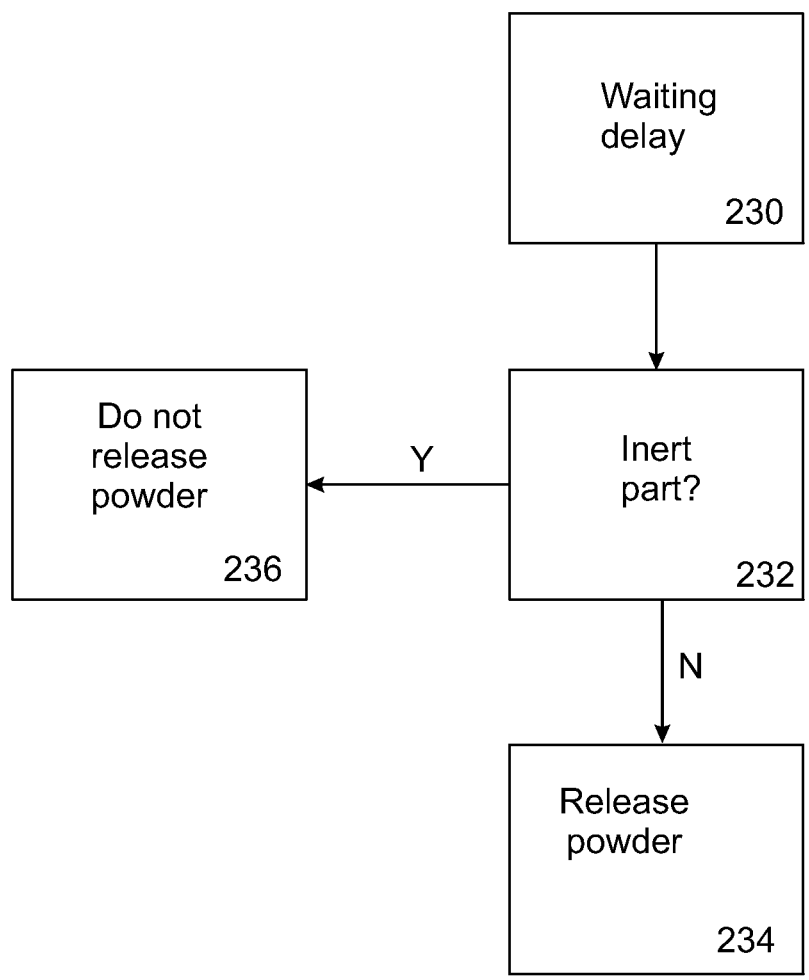
FIG. 2C is a method of releasing an amount of dry powder during a range, in accordance with an exemplary embodiment of the invention.

FIG. 2c is a method of releasing an amount of dry powder 131 during the range, in accordance with an exemplary embodiment of the invention.

At 230, a delay is measured as described herein.

Optionally, at 232, the inert part is detected as described herein.

At 234, powder 131 is released as described herein if the release will not occur during the inert part as described herein.

At 236, powder 131 is not released if the release will occur during the inert part.

Adjusting Doses Based on Feedback

FIG. 12 is a method of adjusting the amount of powder to be delivered based on feedback about the amount actually delivered, in accordance with an exemplary embodiment of the invention. Feedback can be provided by the user and/or by inhaler 101.

At 1201, the amount of powder 131 to be delivered to the patient is determined, for example by a physician prescribing a treatment as described herein. Optionally, one or more parameters of the distribution of the dose over time and/or breaths are provided, for example by calculations, by a look-up table, by manual settings. For example, a relatively large amount of dry powder 131 should be released once a flow rate of 50 liters/minute has been reached, to deliver the set dose over 2 breaths. In order to deliver the dose, the patient would have to generate the required flow rate for a minimum of 0.1 seconds.

At 1203, the amount of powder 131 that was actually delivered to the patient is estimated and/or measured, such as, by measuring the inspiratory flow rate generated by the patient. In a first example, the inspiratory flow may reach a peak of 25 liters/min for a period of 0.1 seconds during the inspiratory period, in which case, no powder would be released. In a second example, the inspiratory flow reached 50 liters/minute, but for a period of only 0.05 seconds, in which case, only half the amount of powder was delivered.

In some embodiments of the invention, the patient can manually press a button to override the programmed settings to adjust the dose released, without having to reprogram the settings. In a third example, a patient continuously receiving low doses of morphine that is not experiencing pain relief fast enough with the current settings can request higher doses without having to reprogram inhaler 101. In a fourth example, powder was released but the patient did not receive the entire treatment properly, such as due to a sudden cough that prevented the entire amount of powder 131 from entering the lungs.

At 1205, the amount of powder 131 that was actually delivered to the patient at 1203 is compared to the amount of powder 131 that was supposed to be delivered at 1201. The difference between the amounts is estimated and/or calculated.

In an exemplary embodiment of the invention, an efficiency (eg. in percent) of delivery of powder 131 is calculated as 'actual dose delivered' divided by 'planned dose'. Optionally, the efficiency is provided to the user as feedback on how to improve performance, for example, as described herein. Optionally or alternatively, the efficiency over one or more treatments is recorded, such as saved to memory. Examples of high efficiency ranges are, 50%-100%, 60%-90%, 65%-75%, or other smaller, intermediate or larger percentages. A potential advantage of recording the efficiency is to analyze treatment patterns over time, for example, a physician and/or patient can look to see if treatment is improving, deteriorating and/or staying the same, with potentially determining how to increase the efficiency. Potentially, a low efficiency suggests a poor compliance with treatment and/or treatment failure.

Optionally, at 1207, the planned amount of powder 131 to deliver during the next breath is adjusted according to the difference estimated and/or calculated as in 1205. The planned amount of powder 131 to be delivered can be increased, decreased and/or unchanged. Referring back to the first and second examples (in 1203), the planned amount of powder 131 to deliver during the next breath can be approximately reduced by 50% (eg. In the first example, the actual flow rate is 25 liters/minute as opposed to a required rate of 50 liters/min; In the second example, the time of the flow rate of 50 liters/min was 0.05 seconds as opposed to the required 0.10 seconds). To deliver the same total dose, the number of breaths during which powder 131 is delivered can be doubled. Referring back to the third example (in 1203), the patient may be allowed to increase the dose until the maximum set threshold. Once the threshold has been reached, the patient will stop receiving morphine. By increasing the dose, the patient eventually to will receive the same amount of morphine but in a shorter time period. Referring back to the fourth example (in 1203), the patient overrides the automatic settings to receive an additional dose in another breath.

Patient Performance Feedback

FIG. 14 is a method of comparing the inhalation pattern of the patient to the inhalation pattern that will potentially result in an improved delivery of powder 131. Feedback is provided in real time to the patient about the performance, for example, to encourage and/or teach improved breathing patterns.

At 1401, the breathing pattern that will potentially provide the greatest percentage of powder delivery to the patient is estimated. Optionally, the inspiratory flow rate range is estimated. For example, as described herein, in order to deliver the largest percentage of powder to the lungs, the flow rate should not be too slow (eg. below 25, 20, 15 liters/min, or other smaller, intermediate or larger flow rates.) and/or too fast (eg. above 70, 80, 90 liters/min or other smaller, intermediate or larger flow rates). The flow rate range to deliver powder can be estimated for example, according to one or more parameters including, patient age, patient weight, disease, disease severity, drug type, powder type (eg. average particle size), target tissue, previous performance by the patient (eg. as previously recorded). The flow rate range can be estimated, for example, by one or more of, calculations, a look-up table, manually entered parameters.

At 1403, the breathing pattern of the patient (eg. inspiratory flow) during treatment (eg. powder 131 delivery) is determined, for example, by using a flow sensor as described herein.

At 1405, the breathing pattern of the patient is compared to the estimated breathing pattern. Optionally, the inspiratory flow rate generated by the patient is compared to determine if the flow rate falls within the estimated range as in 1401.

At 1407, feedback is provided to the patient about the performance as determined in 1405. Optionally, feedback is provided by output interface 121, such as speech, audio and/or visual output. Feedback is provided to encourage and/or teach the patient to breath in the manner that will potentially provide the best treatment. For example, for an adult, if the flow rate is too slow, a fast beep is sounded to encourage the patient to increase the flow rate. If the flow rate is too fast, a slow beep is sounded to encourage the patient to reduce the flow rate. For example, for a child, if the flow rate is too slow, a video and/or image of a smiling face and/or an applauding clown is shown to encourage the child to increase the flow rate. For example, if the flow rate is too slow, the video and/or image can change to a neutral face, or the clown resting.

In some embodiments of the invention, feedback is provided during exhalation, such as to encourage the patient to exhale as much air as possible. For example, a whistle sound and/or an image of an applauding clown while the patient is exhaling. A potential advantage of a prolonged expiratory phase is that higher flow rates and/or volumes can result in the next inspiratory phase, for example, as described herein.

In some embodiments of the invention, speech is provided as feedback to coach the patient, for example, if the patient is breathing properly, a message such as "Great job! Keep it up!" can be played, if the patient needs to increase the flow rate, a message such as "Give it a bit more of a push!" can be played.

Optionally, at 1409, analysis occurs in real time, for example continuously while the patient is breathing. Sampling the flow rate as in 1403 and comparing the flow rates as in 1405 can occur 1, 3, 5, 10, 20 times per second, or other smaller, intermediate or larger sampling rates. The beeps and/or images are optionally updated at the same rate.

Additional Embodiments

Figure 1A:
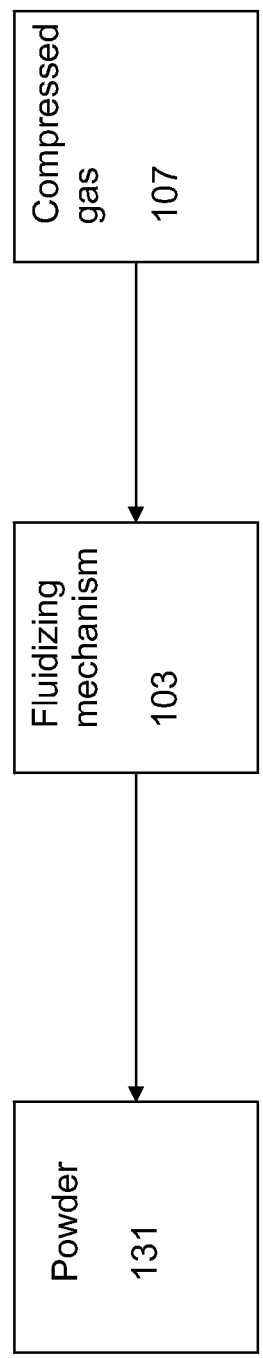
FIG. 1A is a block diagram of the dry powder inhaler, in accordance with an exemplary embodiment of the invention.
Figure 1B:
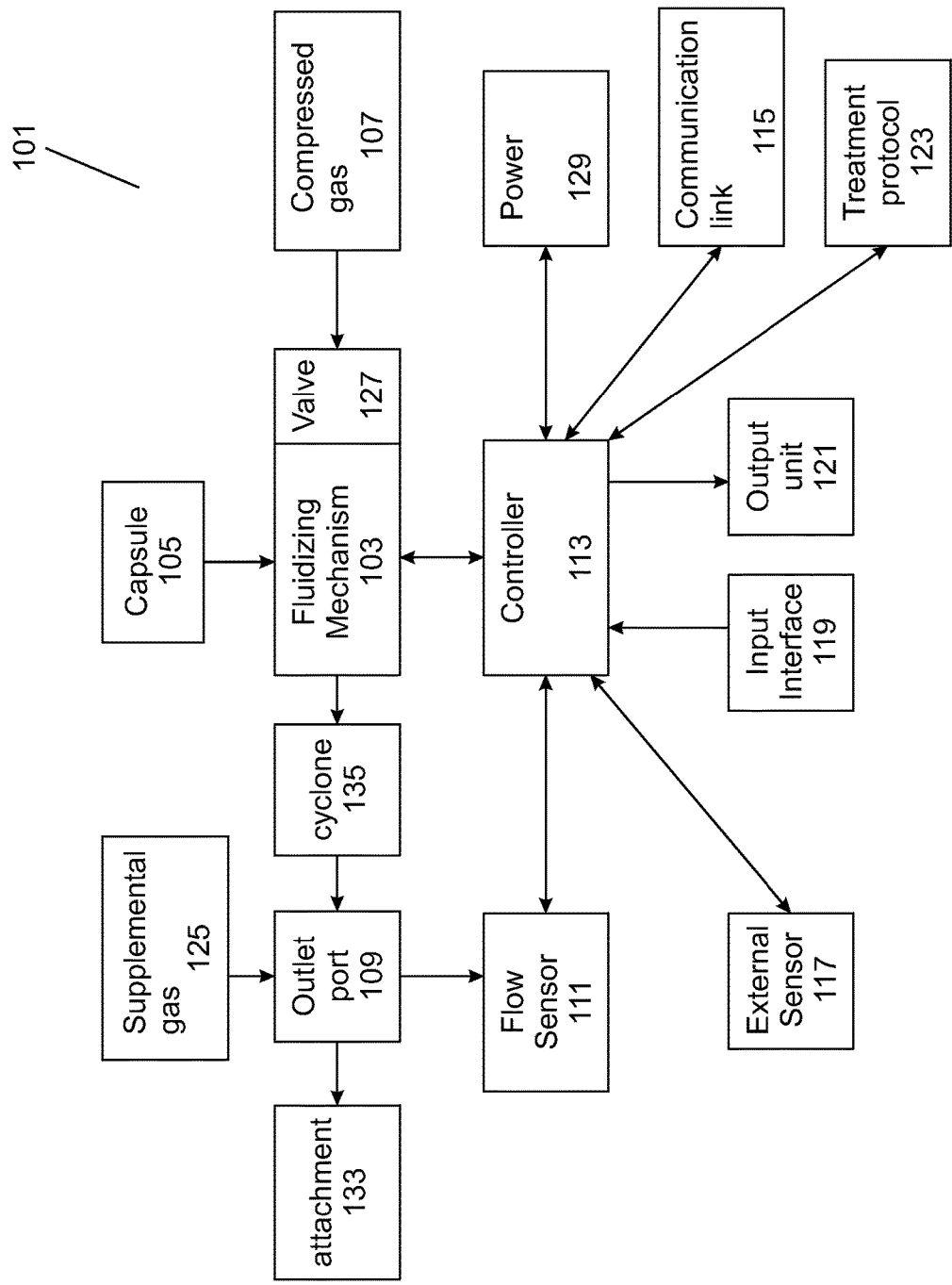
FIG. 1B is a block diagram of the dry powder inhaler in accordance with some embodiments of the invention.

FIG. 1b is a block diagram of inhaler 101 in accordance with some embodiments of the invention Capsule In some embodiments of the invention, capsule 105 comprising dry powder 131 is loaded into mechanism 103. Optionally, capsule 105 is positioned such that one end is in fluid communication with gas 107 and/or the other end is in fluid communication with an outlet port 109.

In some embodiments of the invention, capsule 105 is sealed. Optionally, powder 131 is sterile.

In some embodiments of the invention, capsule 105 is an 'off the shelf' and/or generic capsule, such as capsule 105 manufactured for use with common types of dry powder inhalers, for example a gelatin capsule, a blister and/or foil, a capsule made from a single material with no foil.

In some embodiments of the invention, one capsule 105 is loaded at a time. Alternatively, a magazine of more than one capsule 105 is loaded. Alternatively, a metered dose of powder is provided, such as by a separate mechanism, for example, vibration, static electricity, mechanical transfer.

In some embodiments of the invention, one or more capsules 105 comprising one or more drugs are simultaneously loaded, such that multiple drugs are released.

One or more potential advantages of using powder 131 packaged in capsule 105 include:
 A longer shelf life of the drug due to a more stable state, for example compared to liquid preparations.
 Drug sterility, for example compared to liquid preparations which can serve as a medium for growth of organisms such as *pseudomonas*.
 Powder may not substantially change the temperature of the air the patient breaths in.
 Risk reduction due to improper drug preparation (eg. mixing), as no preparation is required.

Powder

In some embodiments of the invention, an average and/or distribution of the particle size of powder 131 can be set, for example, using calibration data as described herein. For example, the number of holes in capsule 105 can be adjusted to result in the required particle size, such as increasing the number of holes to reduce particle size due to increased deagglomeration of powder 131 by gas 107. Potentially, the average size of powder 131 particles determines the anatomical location where the majority of powder 131 particle end up, and/or the type of particle absorption (local and/or systemic).

Potentially, particles less than 2 micrometers in diameter are inhaled into the lungs, and/or enter the blood circulation, providing for systemic drug delivery and/or treatment of systemic disease. A potential advantage is the replacement of IV drugs. For example: Morphine for pain management, Calcitonin for elevated calcium levels, cancer pain due to Paget's disease and/or osteoporosis, Desmopressin for diseases such as diabetes insipidus, hemophilia A, and/or primary nocturnal enuresis, Insulin for elevated glucose levels.

Potentially, particles in the range of 2-5 micrometers are inhaled into the lungs, producing local treatment effects. A potential advantage is the treatment of lung disorders, for example, salbutamol (eg. asthma), ipratropium bromide (eg. bronchitis, emphysema) antibiotics (eg. respiratory infections).

Potentially, particles larger than 5 micrometers are absorbed in the nasal and/or upper respiratory system, causing local effects. A potential advantage is the treatment of disorders of the nasal and/or upper respiratory area. For example: budesonide (steroid for chronic sinusitis), xylometaoline (decongestant for acute sinusitis), levocarbastine (antihistamine for allergic rhinitis), saline (dry nasal mucosa).

For example, the average particle size for budesonide varies between 4.4 micrometers (eg. if the flow rate of gas used to release powder is at 40 liters/minute) and 7.9 micrometers (if the flow rate is 28 liters/minute).

Additional Features and/or Elements

In some embodiments of the invention, the release of the volume and/or pressure of compressed gas 107 is controlled by a valve 127, for example, as will be described below.

In some embodiments of the invention, powder 131 flows through a cyclone 135 before being released from outlet port 109. Cyclone 135 creates a twisted and/or laminar flow of powder 131. A potential advantage of cyclone 135 is increased deagglomeration. Another potential advantage is reduced particle deposition at the mouth and/or upper airway.

In some embodiments, powder 131 is released suspended in a cloud like formation. Inhalation flow, such as by the patient, moves the cloud formation into the lungs. Alternatively, powder 131 continues to be moved by gas 107 towards the patient, forming a linear and/or straight spine like formation. Alternatively, powder 131 is moved by gas 107 in a spiral like formation, such as after flowing through cyclone 135.

In some embodiments of the invention, one or more attachments 133 are available for outlet port 109, such as a facemask, tube that fits into mouth, tube that fits into one or both nostrils, connection to a mechanical ventilation machine, connection to a ventilation support machine (eg. BIPAP, CPAP), connection to an anesthesia machine. Alternatively, no connection is provided, and/or the patient breaths from a close proximity to the outlet port 109.

In some embodiments of the invention, one or more sensors 111 are used for detecting the release condition, for example, as described herein. Optionally, a flow sensor 111 measures the inspiratory flow rate. Examples of flow sensors include one or more of, a rotary potentiometer, a laminar flow meter, a thermal flow meter, a Coriolis flow meter, an ultrasonic flow meter, a variable area flow meter. Alternatively, sensor 111 detects the vacuum level, for example in outlet port 109. Examples of vacuum sensors include one or more of, a solid state vacuum sensor (analog or digital), a piezo resistive vacuum sensor, a thermocouple gauge tube. Sensor 111 can be located, for example, at port 109, and/or the attachment to port 109 (eg. mask).

In some embodiments of the invention, sensor 111 measures breathing patterns and/or estimates disease conditions and/or severity of disease. For example, sensor 111 can measure expiratory flow rates to generate flow-volume curves. The flow-volume curves can be analyzed to estimate the severity of an obstructive (eg. asthma, COPD) and/or restricted airway disease. Optionally, the improving and/or worsening of the airway disease is used as a feedback to dynamically adjust doses of powder 131, for example, if disease severity is increasing such as reflected by decreasing lung function, a higher dose may be given in smaller amounts spread out over a prolonged period of time.

In some embodiments of the invention, one or more external sensors 117 are used for detecting the secondary release condition, for example, as described herein. Optionally, sensors 117 are an external unit coupled to inhaler 101, such as by a communication link 115, for example, a glucometer, a blood pressure sensor. Alternatively, sensor 117 is physically attached to inhaler 101, such as by a cable.

In some embodiments of the invention, inhaler 101 comprises a controller 113 to control the release of powder, for example, as described herein. Optionally, controller 113 is a programmable chip such as Pic microcontroller or Atmel microcontroller. Optionally or alternatively, controller 113 is an application specific integrated circuit. Optionally or alternatively, controller 113 is a nearby processor configured to perform the functions describe herein, for example a desktop computer, PDA and/or cellphone, such as communicating to inhaler 101 through communication link 115. Optionally or alternatively, controller 113 is located remotely, such as on a central server, communicating to inhaler 101 through link 115.

In some embodiments of the invention, controller 113 comprises a memory portion. Memory portion can have stored thereon, for example, one or more of, software for controller 113, parameters for release conditions, range settings, look-up tables, calibration measurements, and/or saved patient data.

In some embodiments of the invention, controller 113 performs quality assurance, for example, monitoring one or more of, gas 107 flow, particle size, aerosol density, amount of dose delivered. Optionally, one or more quality assurance parameters serve as feedback in adjusting dosage, for example, as described herein.

In some embodiment of the invention, release of powder 131 as described herein occurs according to a treatment protocol 123, for example, by controller 113 executing instructions. Examples of obtaining treatment protocol 123, include one or more of, through an input interface 119 (as will be described herein), from capsule 105 (eg. by barcode, stored on a chip), downloaded from the internet (eg. through link 115), preset by manufacturer. Treatment protocol 123 can be designed for example by one or more of, the patient, a physician, a pharmacist. Treatment protocol 123 can be stored on the memory. Some examples of treatment protocols 123 are provided in the Examples section.

In some embodiments of the invention, an input interface 119 is used to set one or more powder 131 release parameters, for example to program treatment protocol 123 for a patient. Input interface 119 can be in the form of adjustable knobs on device 101, for example, for dose per capsule, treatment dose and/or number of breaths over which to deliver. Optionally or alternatively, input interface 119 is for example one or more of the following: keyboard, touch screen, webpage with login. Optionally or alternatively, input interface 119 is a separate unit coupled to device 101, for example a desktop computer, a laptop, PDA, smartphone. Input interface 119 can communicate with device 101 using an optional communication link 115. A potential advantage is that a physician to can program treatment protocol 123 for a patient remotely, such as using a cellphone.

In some embodiments of the invention, inhaler 101 comprises an output unit 121 for providing data to the user, for example, one or more of, an LCD display, a microphone. Optionally, output unit 121 is the same element as input interface 119. Some examples of messages outputted by output unit 121 include, text such as time and/or number of breaths left for drug delivery, amount of drug delivered, amount of drug remaining, efficiency of delivery, patient instructions (eg. start breathing normally, treatment completed), a beep such as to start and/or stop inhaling, images (eg. a smiling face such as to start inhaling, a frowning face such as if mask was removed during treatment), video (eg. showing instruction on how to inhale), audio (eg. saying to start and/or stop inhaling).

In some embodiments of the invention, inhaler 101 comprises a communication link 115 to transfer data as described herein. Communication link can be wire (eg USB) and/or wireless (eg optical, RF, sonic, ultrasonic).

In some embodiment of the invention, a power source 129 supplies power to one or more of, mechanism to generate compressed gas 107 (as will be described below), fluidizing mechanism 103, controller 113, flow sensor 111, external sensor 117, input interface 119, display 121, communication link 115. Examples of power sources 129 include one or more of, replaceable battery, rechargeable battery, electrical outlet, solar power, chemical energy, manual (eg spring tension created by turning a knob), compressed gas 107.

In some embodiments of the invention, power source 129 is charged before treatment, for example by using a button to charge a battery. Optionally, a beep is sounded once charging has been completed, such as through output unit 121.

In some embodiments of the invention, supplemental gas 125 is delivered in addition to powder 131. Supplemental gas 125 can be used to augment the patient's own inspiratory flow, that is, to 'push' the released powder 131 into the lungs of the patient, for example, in patients that have poor inspiratory flow such as intubated patients and/or bronchoconstricted patients. Flow rates of supplemental gas 125 can vary, for example from 2-100 liters/minute, 10-60 L/min, 20-50 L/min, or other smaller, intermediate or to larger flow ranges.

Data Analysis

A potential advantage of some exemplary embodiments of the invention is the ability of a user, such as the patient and/or physician, to analyze treatment data in order to improve clinical outcomes. For example, in the embodiments in which inhaler 101 comprises data storage, a physician can obtain and/or view data, such as by downloading from inhaler 101 to a laptop, viewing online, viewing on a cellphone. Data can be analyzed, for example, for efficiency of treatment (eg. actual dose delivered compared to dose planned to deliver) and/or for patient compliance (eg. actual treatment plan compared to prescribed treatment plan). A low efficiency of treatment and/or poor patient compliance can potentially be improved by analyzing other data, for example for shallow breathing patterns, by looking for treatment being delivered at incorrect times of the day, verifying that inhaler 101 settings were programmed correctly. By finding the cause of the problem, the physician can re-educate and/or re-coach the patient for improved use of inhaler 101.

Device Calibration

FIG. 3 is a graph of a calibration curve 301, useful in practicing some embodiments of the invention. One or more similar calibration curves can be experimentally measured. The experimental results can be used to estimate the volume and/or pressure of compressed gas 107 to release an amount of powder 131.

Inventors manually pierced four (4) holes at each end of a capsule of Foradil (formoterol fumarate inhalation powder manufactured by Novartis). Foradil is comprised of a dry powder blend of 12 mcg of formoterol fumarate and 25 mg of lactose as a carrier. The pierced capsule was placed in a holding chamber in fluid communication with a source of compressed gas 107.

Inventors released a pulse of three (3) milliliters of room air at two (2) atmospheres of pressure. Twelve (12) pulses of gas were applied in succession to release the powder. The powder and capsule combination was weighed after each release. The remaining drug weight was calculated as the difference between the before and after total weights. The remaining drug weight was plotted as a function of pulse number.

Inventors have discovered an association between the volume and/or pressure of gas, and the amount of powder that can be released from a pierced capsule. As can be seen in graph 301, the association between the remaining drug and an approximately reproducible volume of compressed gas is approximately linear.

Similar device calibration graphs can be constructed from one or more similar experiments, wherein one or more variables are modified, such as one or more of, average powder 131 particle size, distribution of powder 131 particle size, drug type, volume of gas, pressure of gas, piercing mechanism, fluidizing mechanism, number of holes, size of holes, capsule type. For example, one or more calibration curves similar to graph 301 can be created, wherein for each calibration curve the number of holes in the capsule is varied, and the corresponding effect on the average particle size is measured. A potential advantage of one or more calibration curves is to control one or more additional parameters, for example, the inhaler automatically and/or patient manually can vary the number of holes according to the desired average particle size.

In an exemplary embodiment of the invention, the raw measurement data is used to calibrate the inhaler, for example, to estimate values in between two data points. Alternatively, linear functions can be fitted to the experimental data, and the resulting equations can be used by the inhaler to calculate the volume and/or pressure of gas associated with the amount of powder to release.

Exemplary Control of Powder Delivery

FIGS. 7A-F illustrate the ability of the inhaler to control the delivery of dry powder, in accordance with an exemplary embodiment of the invention.

Figure 7A:
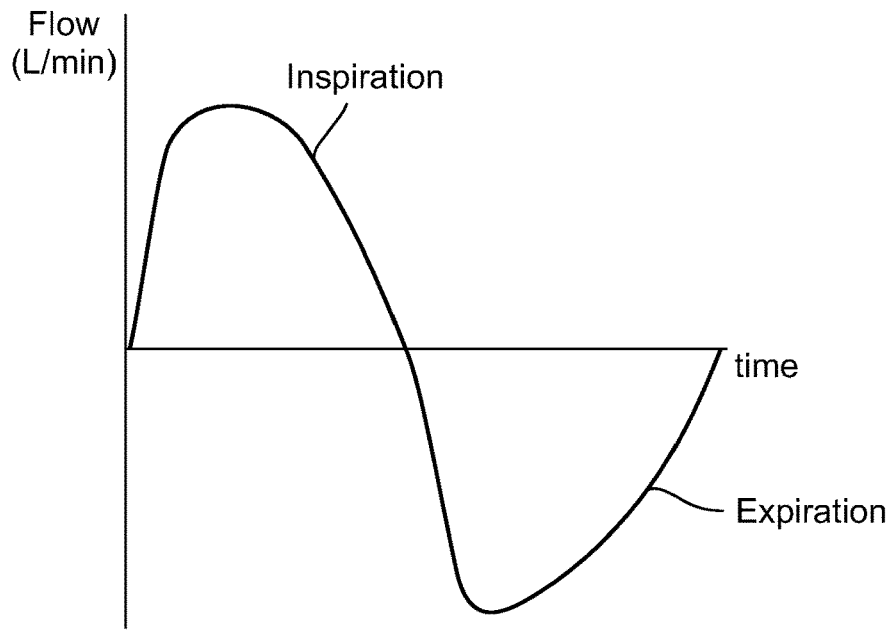

FIG. 7a is an example of a normal flow rate curve as a function of time for a healthy patient during one breath cycle. Such a curve could be measured by flow sensor 111. Inspiratory air flow is positive, expiratory air flow is negative.

In an exemplary embodiment of the invention, the start of the inspiratory phase is estimated and/or calculated, for example, if the start cannot be directly measured and/or detected. Optionally, the start of the inspiratory phase is calibrated to match the to waveform actually measured from the patient, for example, based on sensor sensitivity. Optionally or alternatively, one or more full breath cycles are measured before the release, for example to perform the calibration.

Figure 7B:
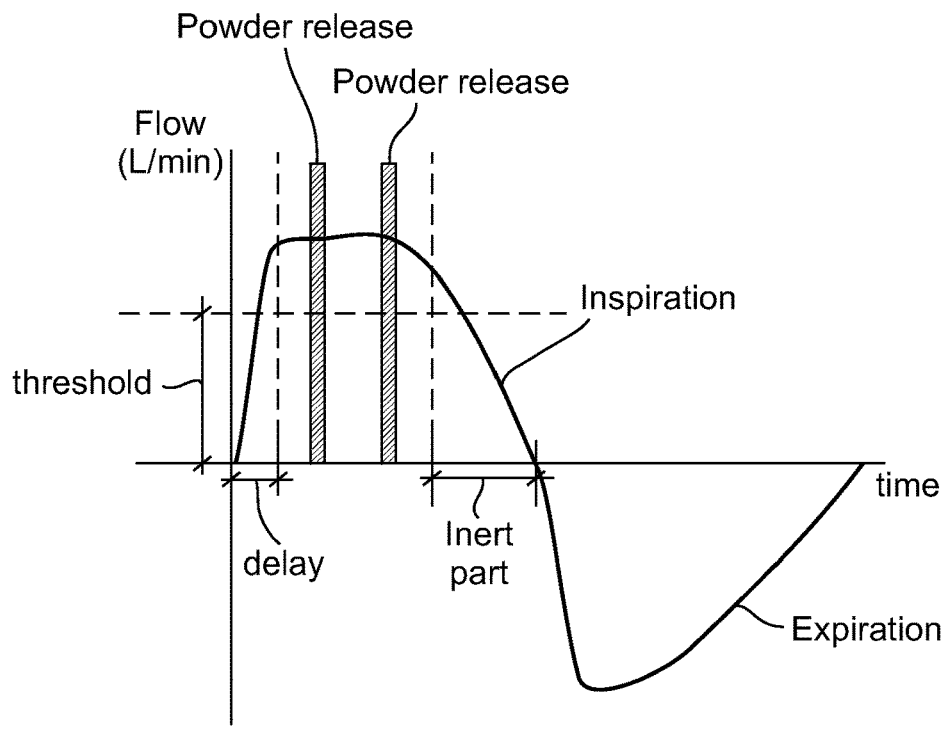

FIG. 7b is an example illustrating one or more release conditions of dry powder delivery as described herein. Shown is a flow "threshold". Inhaler 101 can deliver the dry powder if the inspiratory flow rate exceeds the threshold value, for example, as described herein. Also shown is "delay". Inhaler 101 can deliver a dry powder after waiting the delay from the start of inspiration, for example, as described herein. Furthermore, "inert part" is illustrated.

Inhaler 101 can deliver the dry powder during the inert part and/or not during the inert part, for example, as described herein. Furthermore, shown is the release of two or more amounts of powder during the inspiratory phase, for example, as described herein. Optionally, two or more powder releases are from the same powder source. Alternatively, two or more powder releases are from different powder sources.

Figure 7C:
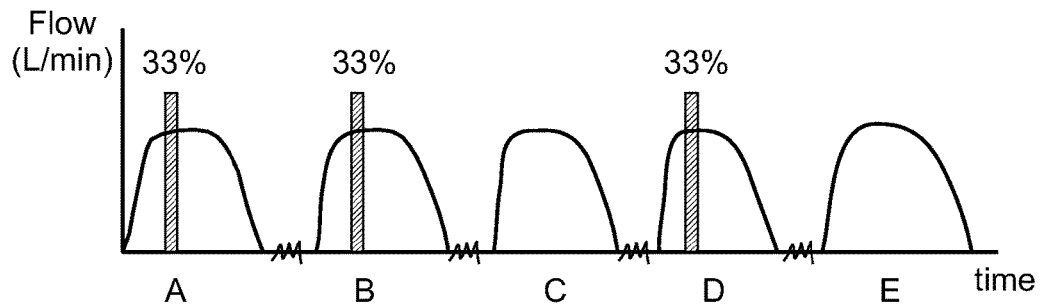
Figure 7D:
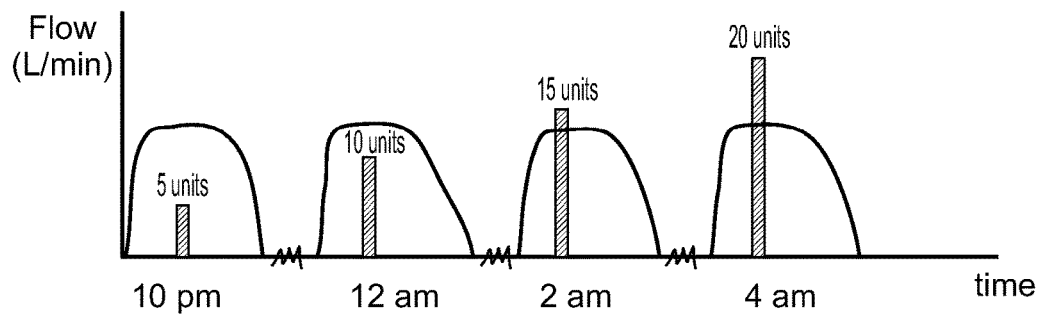
Figure 7E:
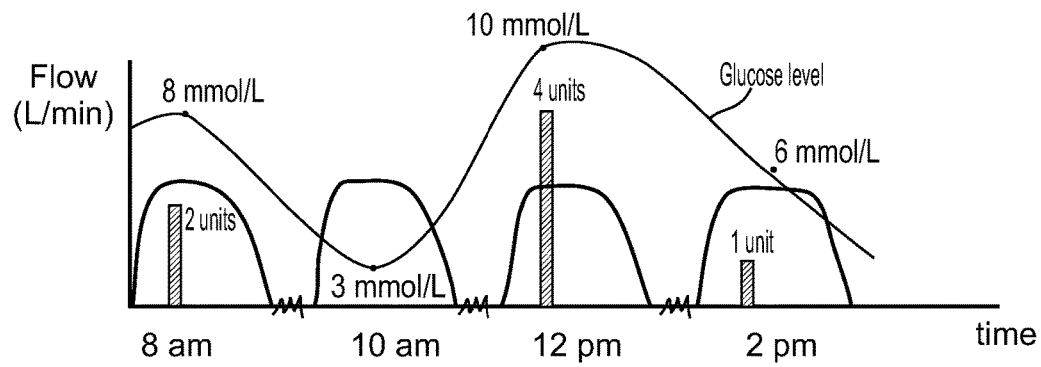

For simplicity, the expiratory phase has been omitted from FIGS. 7C-7E.

FIG. 7C illustrates an example of controlling the release of dry powder according to breath considerations. The dry powder dose to be delivered has been equally split over three breaths. The breaths selected for delivery of 33% of the dry powder per breath are "A", "B" and "D". Breath "C" has been skipped. Breath "E" and later breaths do not receive dry powder as the treatment has ended with breath "D".

FIG. 7D illustrates an example of controlling the release of dry powder according to time considerations. The inhaler has been programmed to release an escalating dose of a drug to a patient, for example suffering from chronic lung disease with progressively worsening lung function during sleep. Patients with chronic lung disease (eg. cystic fibrosis, bronchiectasis, primary cilliary dismotility) may experience progressively worse lung function during the night, such as due to reduced cough and/or mucocilliary clearance. An overnight treatment protocol, such as with sodium chloride and/or bicarbonate may improve morning lung function.

In this example, the inhaler has been programmed to release 5 units of the drug at 10 pm, 10 units of the drug at midnight, 15 units of the drug at 2 am and 40 units of the drug at 4 am.

FIG. 7E illustrates an example of controlling the delivery of inhaled insulin to a to diabetic patient. The diabetic patient is monitored for glucose levels by a glucometer coupled to the inhaler. The number of insulin units delivered is a function of the glucose level. At 8 am, after eating breakfast the glucometer measures a blood glucose level of 8 mmol/L. Inhaler delivers a dose of 2 units of insulin. At 10 am the blood glucose level dropped to 3 mmol/L, so no insulin has been released. At noon, after lunch, the blood glucose level increased to 10 mmol/L, so 4 units have been delivered. At 2 pm, the blood glucose level fell to 6 mmol/L, so 1 unit has been delivered.

Figure 7F:
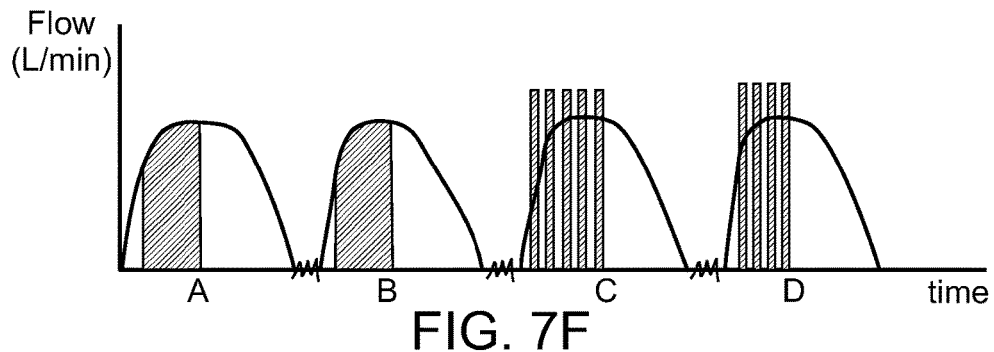

FIG. 7F illustrates an example of the inhaler operating in continuous powder release mode. Breaths "A" and "B" of FIG. 7F illustrate the inhaler continuously releasing dry powder, such as at a relatively slow flow rate, for example 0.5, 1, 3, 5 liters/minute or other smaller, intermediate or larger flow rates, or with closely spaced bursts, for example, 10, 20, 50 bursts per second, or other smaller, intermediate or larger numbers of bursts. Optionally, the release is synchronized to the breaths of the patient. Optionally or alternatively, release occurs after the delay, until just before the inert part. Optionally or alternatively, release occurs during the first part of the inspiratory phase, such as during the first 10%, 30%, 50% or other smaller, intermediate or larger percentages. Alternatively, release occurs during the first 100 ms, 250 ms, 500 ms, 1000 ms, or other smaller, intermediate or larger numbers of milliseconds. The shaded portions indicate the potential amount of drug the patient receives during inhalation.

Alternatively, inhaler releases dry powder in a series of successive releases, as shown in breaths "C" and "D" of FIG. 7F.

A potential advantage of continuous powder release mode and/or the series of successive releases is the delivery of a quantity of powder that cannot be delivered in a single burst.

Exemplary Loading Chamber

FIGS. 8a and 8b illustrate an exemplary design of a loading chamber 847, in accordance with an exemplary embodiment of the invention. FIG. 8a illustrates the placement and optional piercing of a capsule 405 inside fluid mechanism 103. FIG. 8b illustrates an example position of capsule 405 inside chamber 847 such that one or more air currents 807 (optionally generated by gas 107) remove, deagglomerate and/or aerosolize an amount of powder 833 from capsule 805.

In an exemplary design of the invention, capsule 805 is loaded into chamber 847 by placing capsule 805 at the end of a T-shaped loader 859. Loader 859 fits into optional slot 861 of loading chamber 847, so as to provide a correct orientation of capsule 805. Optionally, as loader 859 is pushed down, capsule 805 is pierced by one or more needle wheels 863, for example, two needle wheels 863, one at each end of capsule 805. Optionally or alternatively, capsule 805 is pierced by one or more blades and/or knives (not shown). Optionally or alternatively, capsule 805 is pierced at one or more other locations, for example on the side, to generate an air flow causing swirling of powder particles in order to assist in deagglomeration. Optionally or alternatively, capsule 805 is pierced before being loaded into chamber 847, for example, manually by the patient. Alternatively, capsule 805 is pierced automatically, for example, by controller 113 while inside chamber 847 before the treatment begins. Examples of the number of total holes in capsule 805 include 2, 4, 6, 8, 10 or other smaller, intermediate or larger numbers of holes.

In FIG. 8b, loader 859 has been pushed all the way down, such that capsule 805 lies inside an air tube 865. Air tube 865 is in fluid communication with a source of compressed gas 807 at one end and/or an outlet at the other end.

In an exemplary embodiment of the invention, capsule 805 is removed from inhaler by removing loader 859 from inhaler and removing capsule 805 from loader 859.

Optionally, air tube 865 comprises one or more flanges 867 to prevent migration of capsule 805.

In an exemplary design of the invention, fluidization of powder 833 occurs by air currents 807 flowing through one or more pierced holes 811 of capsule 805. Optionally, air currents 807 flow around and/or outside capsule 805. Alternatively, air currents 807 only flow through one or more holes 811. Air currents 807 remove an amount of powder 833 from capsule 805, deagglomerate and/or aerosolize powder 833, and move powder 833 to the respiratory system of the patient through one or more pierced holes 833 at the opposite end of capsule 805.

In an exemplary design of the invention, powder 833 is removed by a Venturi effect created by air currents 807. Optionally, mechanical vibration and/or oscillation of capsule 805 is used to enhance deagglomeration. Optionally or alternatively, powder is transferred to tube 865 by one or more other methods, for example, electrical charging, mechanical transfer.

In some embodiments of the invention, powder 833 is held in a depression and/or chamber, for example, without capsule 805. A potential advantage of powder 833 in capsule 805 is that capsule 805 can be removed together with any residual powder 833, whereas powder 833 held alone may become adherent to the depression and/or chamber, and/or require special removal in addition to the removal of capsule 805.

Exemplary Mask

FIG. 9 illustrates an exemplary design for a mask 949, in accordance with an exemplary embodiment of the invention. Mask 949 can potentially increase the amount of powder 933 that the patient breaths in, and/or reduce humidity, such as by using one or more valves 953.

In an exemplary design of the invention, mask 949 comprises one or more valves 953, such as a one way valve. Optionally, one or more valves 953 allow expiratory air flow 951, to exit mask 949. A potential advantage is that the humidity in the expiratory air flow 951 does not enter the supply of powder 933.

In an exemplary design of the invention, one or more valves 953 prevent inspiratory air flow 955 from entering from outside mask 949. A potential advantage is that the entire force and/or flow 955 of inspiration can be used to move powder 933 inside the lungs of the patient, such as by directing air currents 907 carrying powder 933.

In an exemplary design of the invention, one or more valves 953 are controlled for example, by controller 413 according to patient inspiration performance. For example, if the inspiratory flow rate is above the upper limit of the range (eg. 80 liters/minute vs. 60 liters/minute), one or more valves 953 can be opened to reduce the effective inspiratory flow rate, such as to below the upper limit (eg. 50 liters/minute). In another example, if the inspiratory flow rate is below the lower limit of the range (eg. 10 liters/minute vs. 20 liters/minute), one or more valves 953 can be closed to increase the effective inspiratory flow rate, such as to above the lower limit (eg. 30 liters/min)

Exemplary Inhaler Designs

Figure 4A:
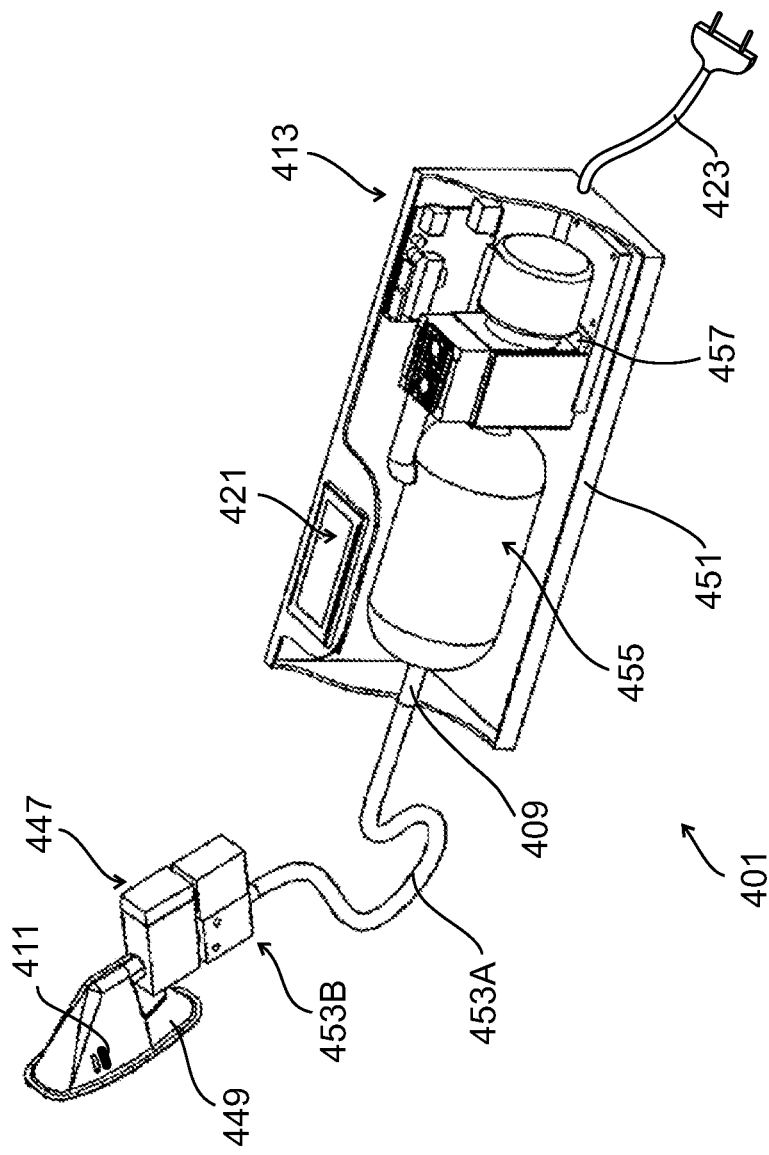
FIGS. 4A and 4B illustrate an exemplary desktop inhaler design, in accordance with an exemplary embodiment of the invention.
Figure 4B:
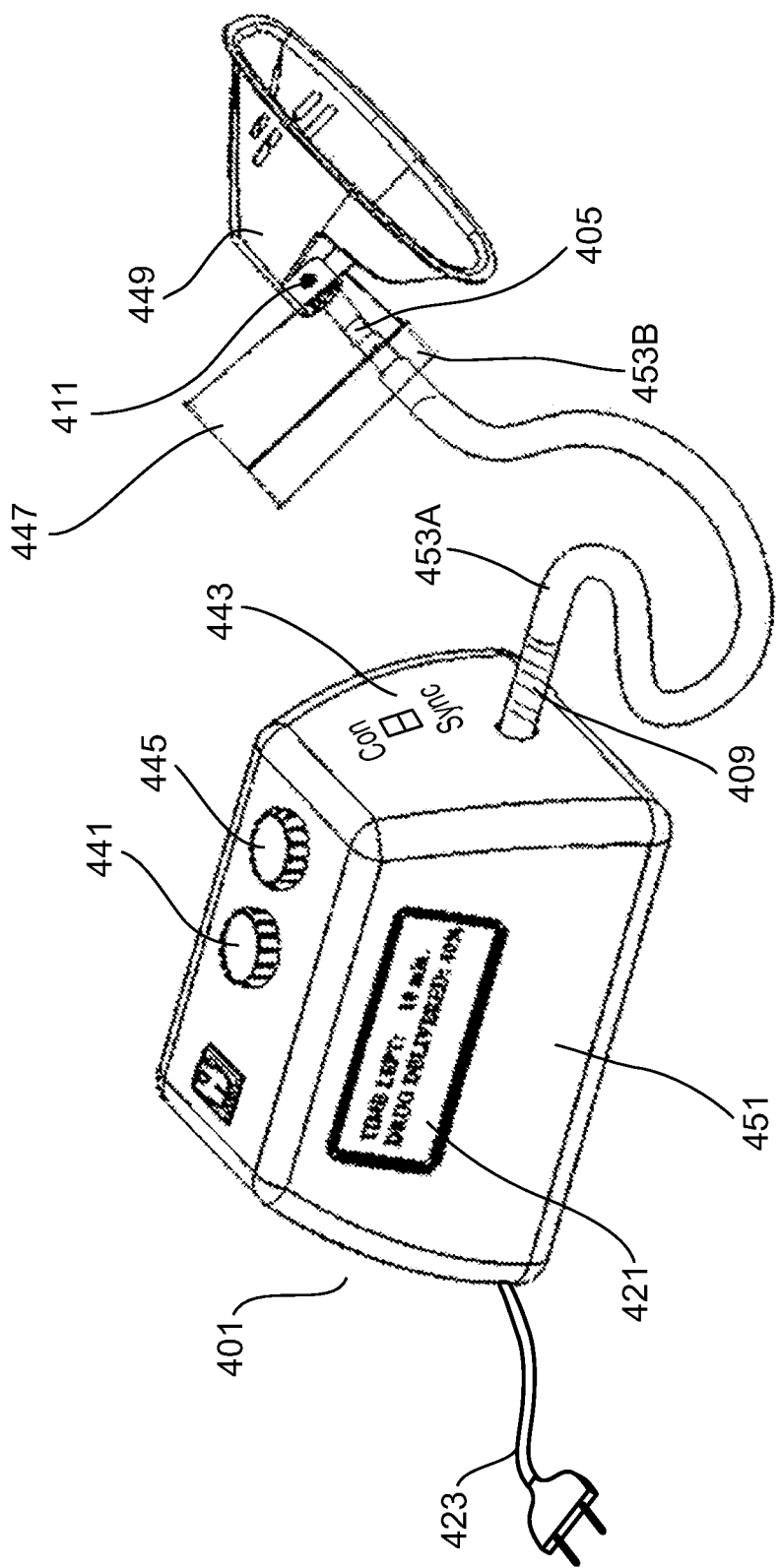

FIGS. 4a and 4b illustrate an exemplary desktop inhaler 401 design, in accordance with an exemplary embodiment of the invention. The design of inhaler 401 is for example, for one or more of, a room in a home, hospital ward, emergency room, ambulance, clinic. FIG. 4a illustrates an exemplary design of inhaler 401, showing internal elements. FIG. 4b illustrates an exemplary design of inhaler 401, showing external features.

In an exemplary design of the invention, inhaler 401 weighs for example, between 500 grams and 10 kilograms, between 1 kg and 5 kg, between 2 kg and 4 kg, or other smaller, intermediate or larger ranges of weights.

In an exemplary design of the invention, capsule 405 comprising dry powder 131 is loaded into loading chamber 447 as previously described. Optionally or alternatively, a magazine of one or more capsules is loaded into a chamber. Optionally or alternatively, the dry powder is located inside a blister covered with foil. Optionally or alternatively, dry powder (without a capsule) is loaded into a metering chamber. Loading chamber 447 can be located, for example, between an attachment such as a mask 449 (optionally at the end of a tube 453A) and an outlet port 409. Alternatively, loading chamber 447 is located anywhere along tube 453A. Alternatively, loading chamber is located inside a main compartment 451 of inhaler 401.

In an exemplary design of the invention, device mode switch 443 can be set to continuous flow mode and/or to breath synchronized mode as described herein.

In an exemplary design of the invention, one or more knobs are used to adjust inhaler 401 settings, optionally depending on the mode set according to switch 443. Optionally, in the case of breath synchronized mode, knob 441 and/or knob 445 respectfully control the volume and/or pressure of compressed air used to fluidize the contents of capsule 405 per breath, as described herein. Optionally or alternatively knobs 441 and/or 445 can be used to set the number of pulses, the delay and/or the threshold value as described herein. Optionally or alternatively, for example, in the case of continuous flow mode, knob 441 and/or knob 445 respectfully control the flow rate (eg. in liters per minute) and/or pressure of compressed air. Optionally or alternatively, one or more additional knobs can control one or more other parameters, for example, as described herein. Alternatively, there are no knobs on the device, programming occurs by another interface as described herein.

A potential advantage of knobs such as 441 and/or 445 is quick and easy setup and/or configuration, such as by busy emergency room personnel. For example, a physician can prescribe a certain medication, and then specify the pressure, volume and/or flow rate settings according to the dose and/or length of treatment.

In an exemplary design of the invention, a facemask 449 (such as described with reference to FIG. 9) is attached to end of optional tube 453A. Facemask 449 can be comfortable to wear and easy to use by most patients, for example small children and/or the elderly. Optionally, tube 453A is attached to port 409. Alternatively, other connections as described herein can be attached to outlet port 409.

In an exemplary design of the invention, one or more flow sensors 411 are connected to facemask 449. Alternatively, flow sensor 411 is located for example in one or more of, outlet port 409, loading chamber 447, valve 453B. Flow sensor 411 measures the inspiratory flow rates, for example, as described herein. Optionally or alternatively, one or more other sensors, such as a glucometer, are utilized as described herein.

In an exemplary design of the invention, a controller 413 and/or pressostat (not shown) monitor the inspiratory flow rate using sensor 411. Controller 413 determines the point at which powder should be released to the patient, for example, according to the parameters and/or thresholds as described herein. Controller 413 releases the set volume and/or pressure of compressed gas to fluidize powder in capsule 405 as described herein.

In an exemplary design of the invention, inhaler 401 comprises a compressor 457 for generating compressed gas to release powder 131 in capsule 405. Compressor 457 pumps gas (eg. room air, heliox, oxygen) into an air tank 455, through an optional filter (not shown). An optional air dryer (not shown) removes moisture. The pressure in the air tank 455 is measured by a pressure sensor (not shown). Controller 413 monitors the pressure in tank 455 and turns compressor 457 on and off accordingly. The pressure in tank 455 is set and/or maintained to release a set amount of dry powder 131, for example, as described herein. The pressure in tank 455 can be constant for the entire duration of treatment. Alternatively, a pressuring regulating valve (not shown) can be used to decrease the pressure and/or apply different pressures, such as to change the amount of dry powder to deliver between breaths.

A potential advantage of tank 455 being much larger than the air volume required to release the powder is that the pressure in the released air is approximately constant throughout the release. Another potential advantage is that tank 455 can be filled with enough air for the entire treatment and/or most of the treatment. An example of the volume of tank 455 is 50 mL, 150 mL, 300 mL, 500 mL, 1 liter, or other smaller, intermediate or larger volumes.

In an exemplary embodiment of the invention, a valve 453B controls the volume of air released from tank 455. Optionally, valve 453B is a solenoid valve. Valve 453B is located before chamber 447, for example close to chamber 447 (as shown), or alternatively, further from chamber, such as at port 409. The volume of released air is used to release the amount of powder from capsule 405 in chamber 447, for example, as described herein. Optionally, controller 413 regulates the volume of air released from tank 455 by varying the time that valve 453B is open, for example, by using a look-up table comprising calibration data, by calculation, by measuring the air released such as by a sensor. Alternatively, valve 453B is opened and/or closed manually, such as by pressing a button.

In an exemplary design of the invention, a visual display 421 shows the approximate time left in the treatment session and/or the amount of drug delivered (eg. by percent, by weight). Optionally or alternatively, one or more other parameters associated with the treatment session, for example, as described herein, are shown. Optionally or alternatively, other types of feedback can be used, such as audio feedback, for example, as described herein.

In an exemplary design of the invention, a power plug 423 provides electrical power to inhaler 401. Optionally or alternatively, inhaler 401 comprises an internal battery that is chargeable, such as by plug 423.

Portable Version

Figure 5:
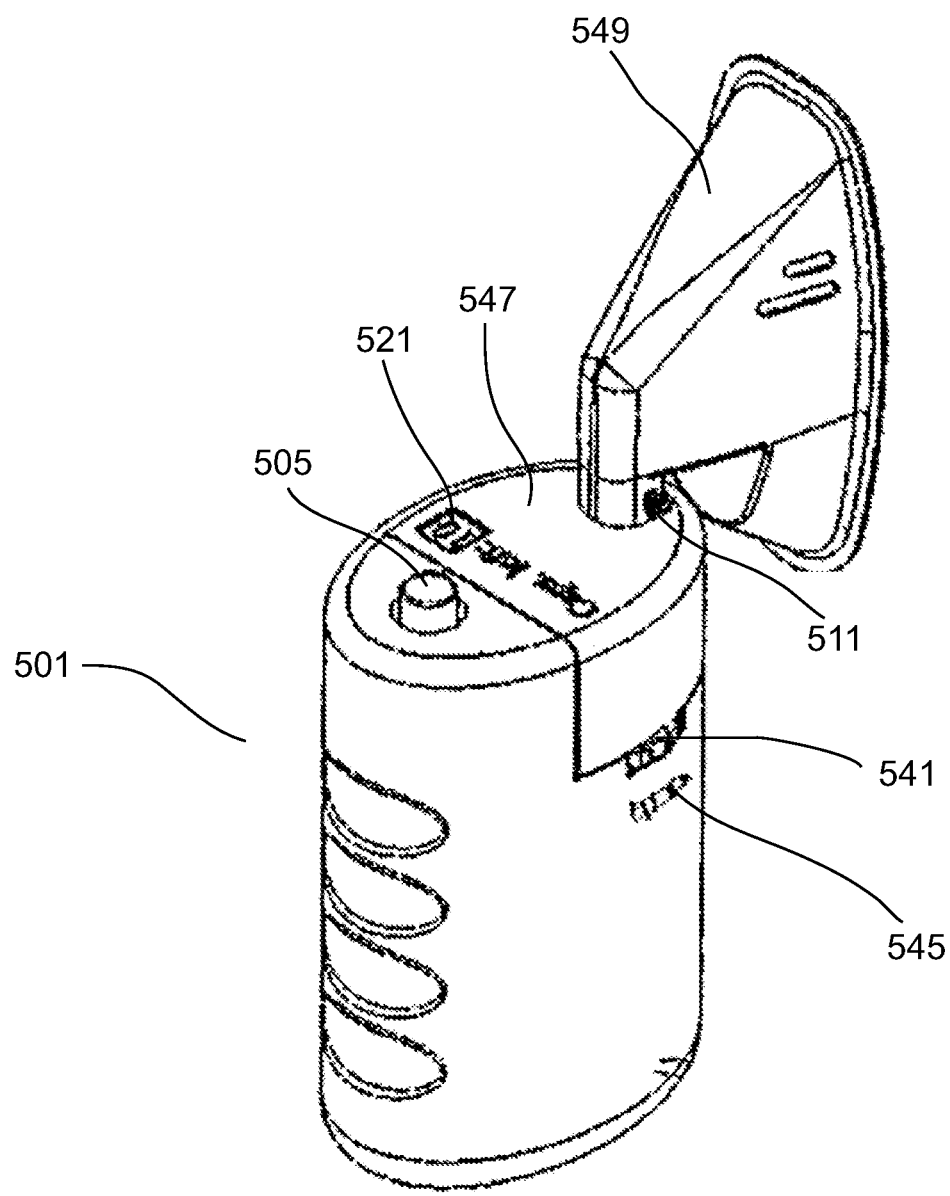
FIG. 5 illustrates an exemplary portable inhaler design, in accordance with an exemplary embodiment of the invention.

FIG. 5 illustrates an exemplary portable inhaler 501 design, in accordance with an exemplary embodiment of the invention. Inhaler 501 is similar to inhaler 401 of FIG. 4. Elements have been numbered in a corresponding manner.

An exemplary portable inhaler 501 is self-powered, for example, comprising a portable power source such as a battery and/or being easy to plug in such as to recharge the battery.

An exemplary portable inhaler 501 comprises a chamber and/or a tank to store a sufficient supply of gas for 5, 10, 50, 100 releases of powder, or other smaller, intermediate or larger numbers of releases. The chamber and/or tank is optionally rechargeable, for example, by plugging in to an external source such as a gas tank.

An example of a patient that may benefit from the portable inhaler is an asthma sufferer that wants to continue normal daily function.

Inhaler 501 can be made compact, for example, by a small source of compressed gas. One or more such sources will be described below.

In an exemplary embodiment of the invention, inhaler 501 weighs for example between 0.1 kg and 2 kg, between 0.2 kg and 1 kg, or other smaller, intermediate or larger ranges of weights.

Alternative Designs of Compressed Air Sources

Figure 6A:
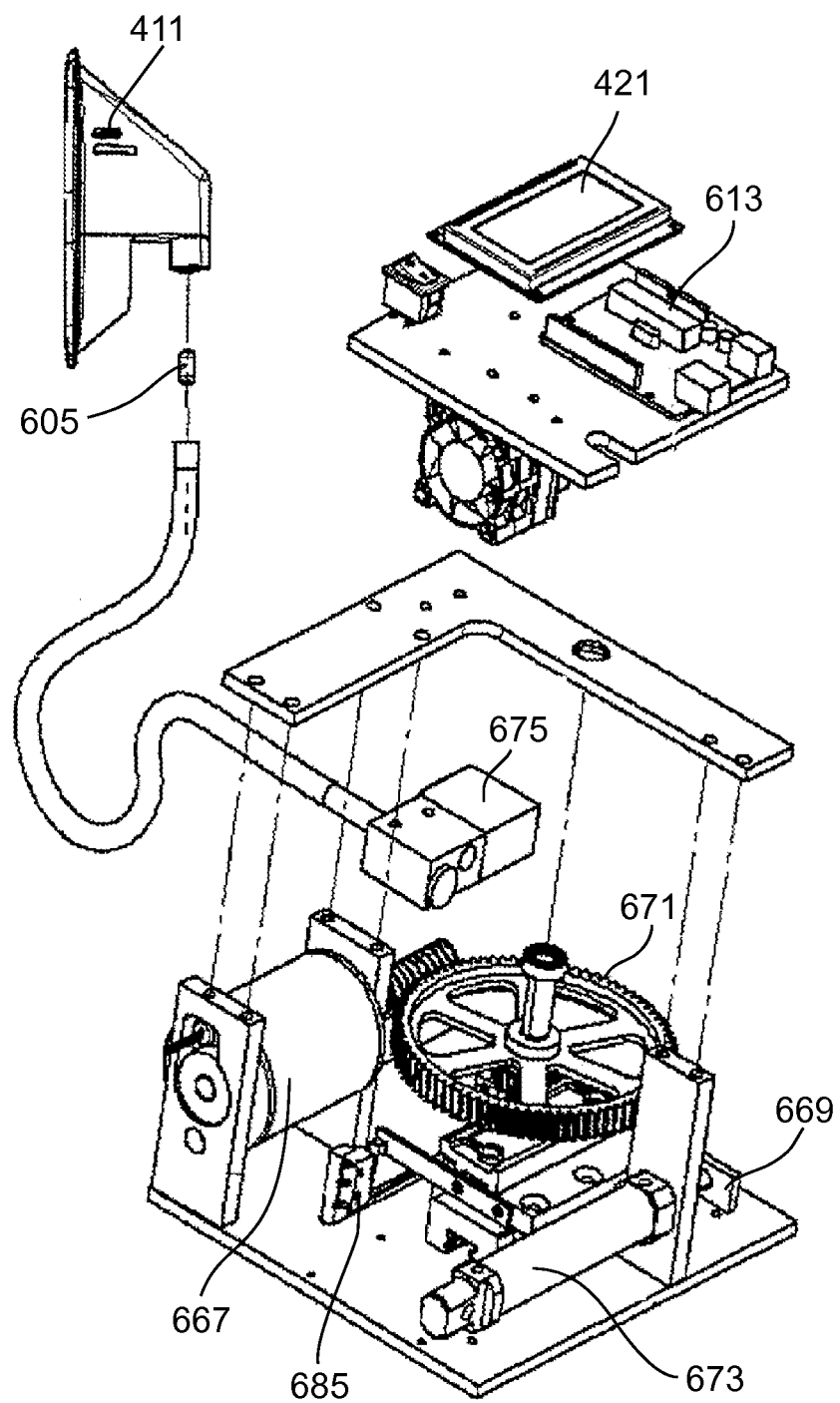

FIG. 6a illustrates an exemplary design of a source of compressed gas 107 that can deliver a specified volume and/or pressure of gas 107 to release powder in capsule 605, for example, as described herein. An electric motor 667 moves a piston 669 by rotating a gear 671. Piston 669 compresses air in cylinder 673, thereby increasing the pressure of the compressed air. Optionally, the pressure inside cylinder 673 is monitored by a pressure sensor (not shown). Optionally, controller 613 regulates the movement of piston 669 to reach the required pressure inside cylinder 673, for example, by piston 669 contacting a limit switch 685, switch 685 provides a feedback to controller 613 to stop the movement of piston 669. Optionally or alternatively, piston 669 is manually operated, for example, as will be described below, thereby potentially reducing and/or eliminating the need for the power source.

Optionally, a valve 675, such as a solenoid valve, controls the release of the required volume of air from cylinder 673, for example, as described herein.

In an exemplary design, piston 669 refills cylinder 673 at a rate sufficient to meet powder release rates. Optionally, cylinder 673 is refilled after every breath, for example if cylinder 673 is sufficiently small, such as 1 milliliter, 3 mL, 5 mL, or other smaller, intermediate or larger volumes of air.

In an exemplary design, a pressure sensor (not shown) displays the air pressure inside tank 455, for example by one or more of, pressure gauge, audio message, beep, display 421. Air is pumped (eg. by one or more methods as described herein) until the supply of gas 107 is sufficient for the entire duration of treatment. Feedback such as one or more of an audio beep, an audio message, a visual display 421, a green light, signals when to stop pumping and/or when to start pumping again (eg. gas 107 needs to be replenished).

Figure 6B:
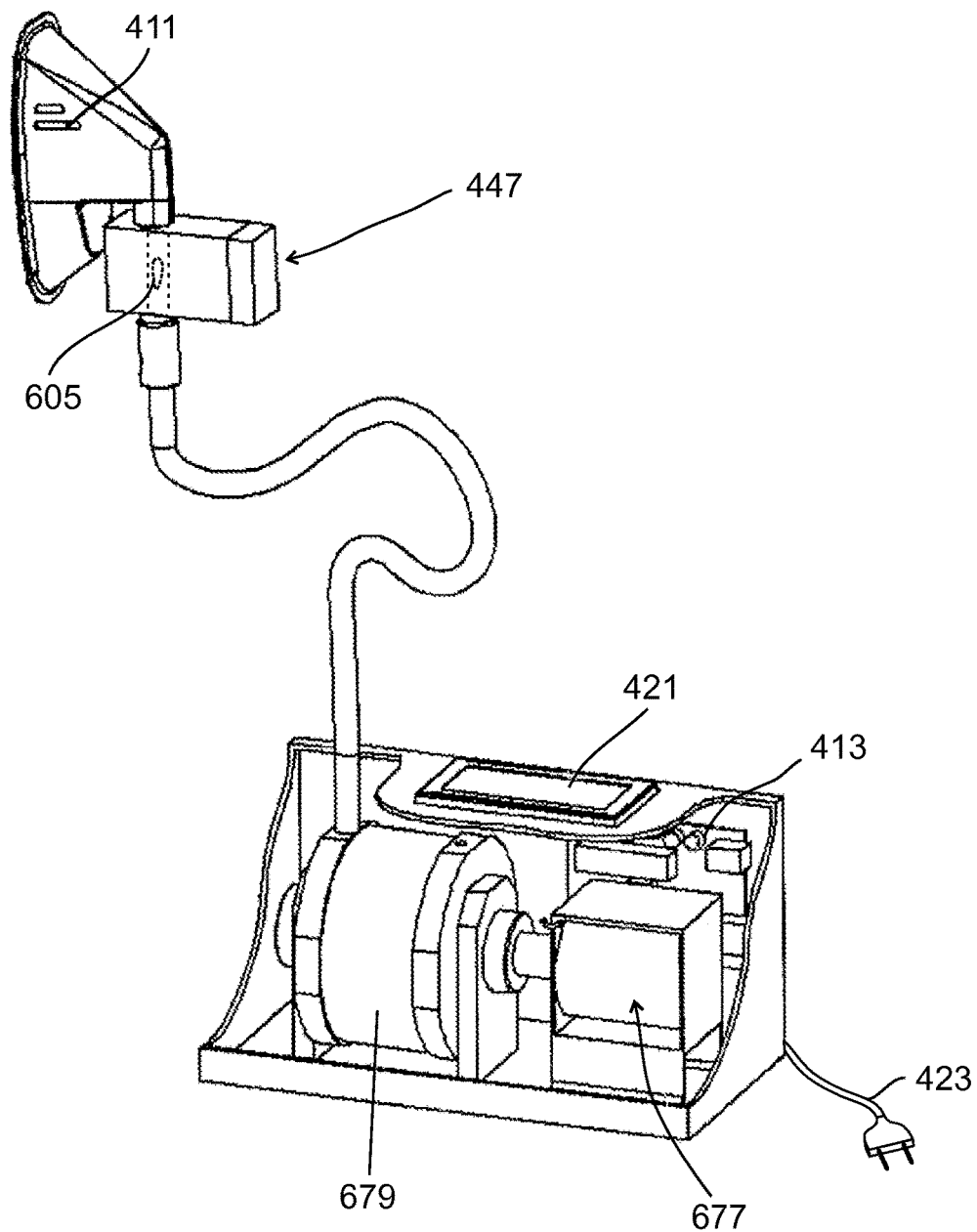

FIG. **6*b* illustrates an alternative design of a source of gas 107 using a solenoid actuator 679 activating a piston 677. Optionally, actuator 679 is controlled by controller 613. Alternatively, actuator 679** is manually activated, such as by patient.

A potential advantage of using a solenoid actuator 679 is that compressed gas 107 is generated to the specified volume and/or pressure at about the moment it is needed to release the powder. The volume and/or pressure of gas 107 can be changed from breath to breath by control of actuator 679. Gas 107 releases powder approximately as soon as the gas 107 is generated, therefore the storage tank is not necessary. A potential advantage of a configuration of actuator 679 and/or piston 677 is that the configuration is small enough to fit inside a portable inhaler.

Figure 6C:
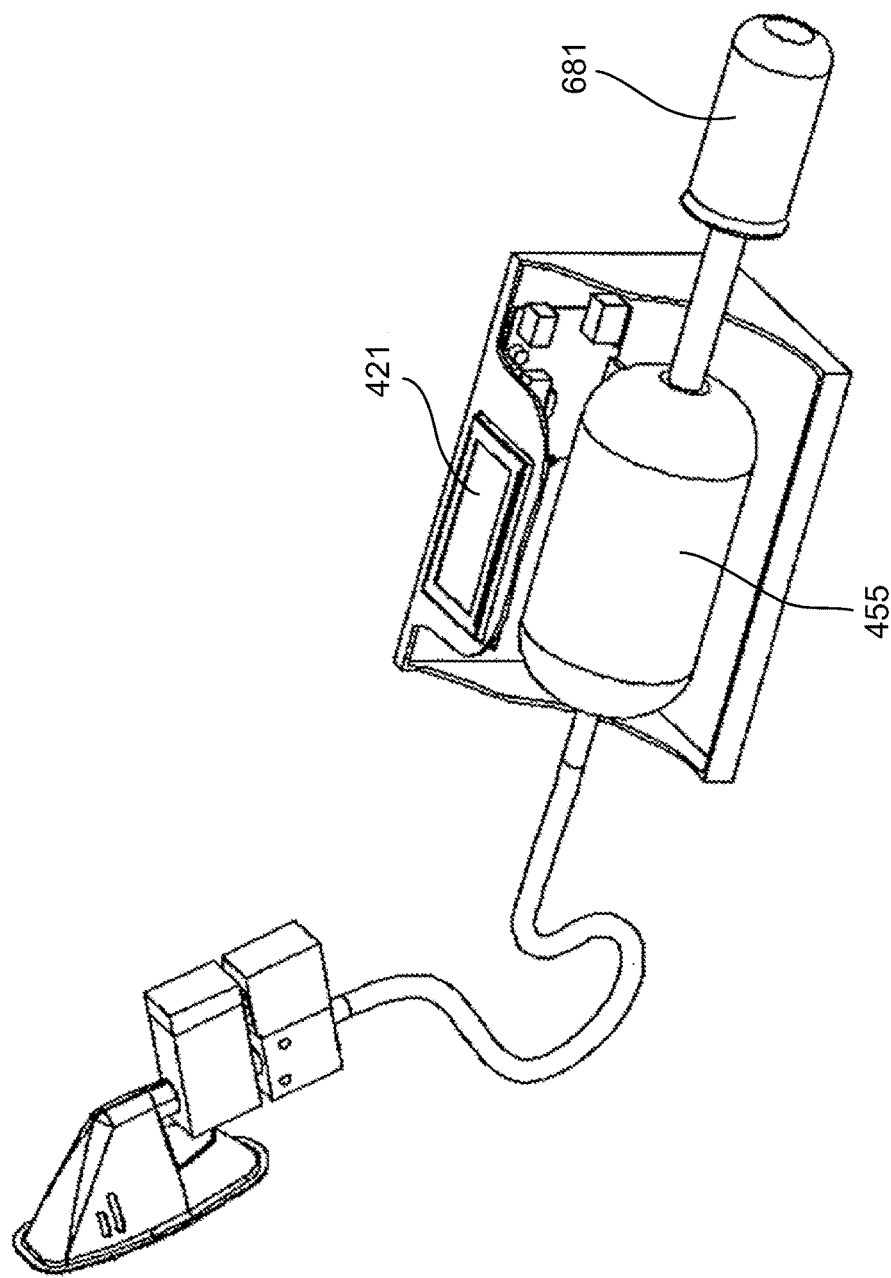
Figure 6D:
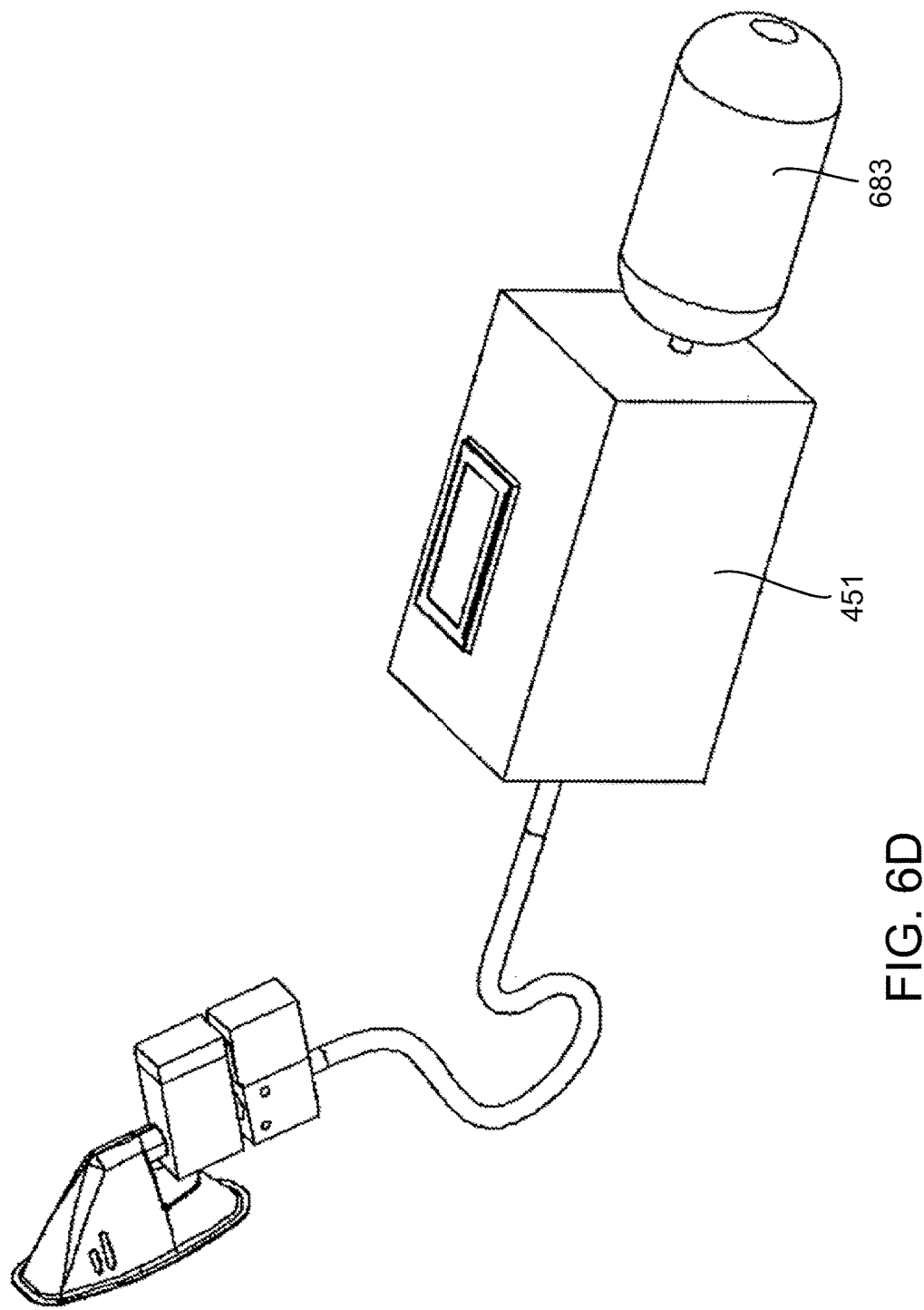

FIG. **6*c* illustrates an alternative design of a source of gas 107 using a handpump 681. A user, for example, one or more of, the patient, a caregiver, a physician, moves handle of pump 681 back and forth to generate a source of gas 107 (eg. room air). Optionally the gas moves through a one way valve (not shown) and is stored in tank 455**.

FIG. **6*d* illustrates an alternative design of a source of gas 107 using an external gas tank 683. Optionally, external gas tank 683 is temporarily connected to body of inhaler 451 to fill up tank 455. Alternatively, external tank 683 is connected to body of inhaler 451 serving as the source of gas 107, for example, for one or more of the treatment, part of the treatment, the entire treatment, one or more treatments until gas 107** runs out.

In an alternative design, controller and/or valve control the release of gas 107 as described herein.

In an alternative design, a pressure sensor (not shown) measures the pressure inside tank 683. Feedback (as described herein) is provided when gas 107 needs to be replaced.

Alternative Number of Chambers

FIG. 10 illustrates an embodiment having two loading chambers 447A and 447B, in accordance with an exemplary embodiment of the invention. Use of two chambers allows for two capsules, optionally comprising two different drugs to be used. Alternatively, both capsules comprise the same drug.

In an alternative design, chambers 447A and/or 447B are parallel to one another. Optionally, both powders are released at substantially the same time. For example, the volume and/or pressure of gas 107 released as described herein is adjusted such that the proper amount of powder is obtained from both capsules (eg. calibration as described with reference to FIG. 3). Alternatively, powders are released at different times, for example, by a switch (not shown) set to control the flow of gas 107 through one chamber 447A and/or the other chamber 447B.

In some embodiments, chambers 447A and/or 447B are in series with one another. Optionally, release of gas 107 releases powder from both capsules, for example, after being calibrated as described herein.

Although two chambers are shown, this is for illustration purposes only, as the embodiment is not limited to two. Other numbers of chambers can be used, for example, 3, 5, 7 or other smaller, intermediate or larger numbers of chambers. Alternatively, one chamber 447 can be used with positions for two or more capsules, optionally different capsules. For example, chamber 447 can hold 3, 5, 7, or other smaller, intermediate or larger number of capsules.

All Mechanical Embodiment

FIG. **11*a* is an all-mechanical design of an exemplary embodiment of inhaler 401, such that no electricity is required for operation. FIGS. 11*b*, 11*c* and 11*d* illustrate the operation of a design of the source of gas 107**.

In a mechanical design, one or more parameters are set and/or adjusted using knobs (not shown) as described herein. For example, the volume and/or pressure is set.

As shown in FIG. **11*b*, a handle 1181 is connected to a piston 1169 inside a chamber 1173. As handle 1181 is pulled back, a spring 1185 stores the created tensile force. Optionally, a valve such as a one way valve (not shown) allows air (eg. room air) to enter chamber 1173. The length that handle 1181 can be pulled back is determined by a pinion 1183, thereby controlling the volume of air inside chamber 1173. Pinion 1183 prevents movement of handle 1181** past a volume and/or pressure, such as set by one or more knobs.

In a mechanical design, sensor 1111, detects a release condition. Optionally, sensor 1111 is a flow sensor, for example, a sail, a vane, a flap, a second stage regulator (eg. as used in scuba diving gear). Upon the detection of the release condition, sensor 1111 triggers pinion 1183 to release handle 1181. As shown in FIG. **11*c*, tensile force in spring 1185 causes handle 1181 to move forward, causing piston 1169 to compress air inside chamber 1173**.

Optionally, piston 1169 moves valve 1187, causing release of air 107 through an outlet port 1109. Alternatively, valve 1187 is released by another mechanism, for example, by a button.

The all mechanical design is not limited to the embodiment described herein. Optionally, one or more elements of the embodiments described herein can replace one or more elements of the mechanical design, for example, using a handpump to fill a tank, attaching a source of external gas 107, and/or a mechanical sensor for triggering the release of gas 107.

KIT

FIG. 13 is an illustration of an exemplary kit 1301, in accordance with an exemplary embodiment of the invention. Kit 1301 is designed to be commercially marketed. Kit 1301 comprises one or more required components for personal use, for example, portable inhaler 1303 with facemask 1315, electrical outlet charger 1305, battery 1307, mouth adapter 1309, nasal adapter 1311 and/or capsule magazine 1313.

Sample Instructions for Using Kit:

Place battery 1307 into inhaler 1303. If battery 1307 is rechargeable, charge to battery 1307 using charger 1305. If power is a gas source, attach the gas source to inhaler 1303. Insert one or more capsules of dry powder into container (eg. capsule magazine) 1313. Insert capsule magazine 1313 into inhaler 1303. Inhaler 1303 is preassembled with facemask 1315, however for convenience, facemask 1315 can be replaced with mouth adapter 1309 or nasal adapter 1311. Mouth adapter 1309 may be more comfortable to use. Nasal adapter 1311 can allow for talking while using inhaler 1303 and/or to direct treatment to the nasal cavity.

In some embodiments of the kit, the kit comprises only parts (eg. without inhaler 1303), for example, capsule magazine 1313 and battery 1307. Optionally, battery 1307 is embedded in capsule magazine 1313.

In some embodiments of the invention, the medicament is readable by a reader in inhaler 1303, by being packaged together for example, with one or more of, an RFId, barcode, EEPROM. Optionally, one or more of, for example, the treatment protocol, thresholds, safety parameters are read to control the release of powder accordingly.

Adjusting for Pressure Changes

In an exemplary embodiment of the invention, inhaler 101 adjusts the release of powder 131 according to dynamic pressure conditions. In some embodiments, pressure of released air 107 is highest at the start of the release, subsequently falling, for example, in a piston and cylinder configuration. In some embodiments, pressure of released air 107 increases after release to a maximum and subsequently falls, for example, in a solenoid and cylinder configuration.

In an exemplary embodiment of the invention, inhaler 101 measures and/or estimates the amount of powder 131 released and/or the changing pressure conditions, for example, by one or more of, pressure sensors, sensors to detect particles, performing calculations, use of pre-calibrated look-up tables. Inhaler 101 compares the actual (eg. measured and/or estimated) powder 131 released to the planned amount of powder 131 to release. Any differences are reflected by changes to the subsequent release of powder 131. For example, if too much powder 131 was released, the next release of powder 131 will be reduced by an approximately similar amount.

It is expected that during the life of a patent maturing from this application many relevant dry powder inhalers will be developed and the scope of the term inhaler is intended to include all such new technologies a priori.

As used herein the term "about" refers to ±10%. The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following prophetic, worked out, examples, which together with the above descriptions illustrate some embodiments of the invention in a non limiting fashion.

Example 1

Child with Asthma

A 4 year old boy weighing 20 kg with severely uncontrolled asthma arrives at a physician's office for a routine visit. The child is currently prescribed budesonide 400 mcg 3 times daily using conventional treatment with a MDI with a spacer. Treatment compliance has not been adequate due to the refusal of the child to adhere to the mask. The parents have become frustrated by trying to deliver the treatment to a screaming and crying child.

The physician changes the treatment to budesonide 400 mcg 2 times daily using an exemplary embodiment of the invention with a facemask attachment. The daily dose has been reduced due to a higher expected treatment efficiency.

The physician enters the following parameters with the goal of powder delivery as quickly as possible:

Weight of child=20 kg
Start delay=5% of tidal volume. (Tidal volume is automatically estimated according to weight, at 10 milliliters per kilogram)
Inert part=50% of tidal volume.
Optional setting=release after a prolonged exhalation
Number of breaths during which to deliver treatment=1 (To enhance treatment compliance)
Inspiratory flow threshold=20 liters/min
Dose per capsule=400 micrograms
Dose to deliver per treatment=400 micrograms (number and/or percent of capsule to To deliver treatment, the parents place the mask on the child. The child breaths erratically while crying and screaming. Release parameters are continuously monitored, and powder is released when conditions have been met, for example, during a deep breath before a scream. The amount of powder released is estimated. If the full dose of powder has not been delivered during a single breath, the remaining powder is delivered during one or more additional breaths.

Example 2

Adult with Cystic Fibrosis

A 30 year old patient with cystic fibrosis has been prescribed treatment with hypertonic saline 7% 4-5 ml 3 times daily. Each inhalation requires about 20-30 minutes. The patient is non-compliant with treatment due to a very busy daily schedule with insufficient time available for treatments.

Overnight treatment of powdered (1-3 micrometer diameter particles) salt (sodium chloride) is prescribed using an embodiment of the present invention.

The physician enters the following parameters with the goal of prolonged treatment of low doses to reach as deeply as possible into the respiratory system:

Weight of patient=70 kg

Start delay=1% of tidal volume. (Tidal volume is automatically estimated according to weight, at 10 milliliters per kilogram)

Inert part=30% of tidal volume. (The first 30% of the inspiratory volume enters the deepest parts of the lungs)

Number of hours during which to deliver treatment=5

Inspiratory flow threshold=0.5 liters/min

Dose per capsule=100 milligram

Dose to deliver per treatment (5 hours of sleep)=100 milligrams (dose equivalent to inhalation therapy)

To deliver treatment, the patient uses a nasal cannula attachment. Approximately equal amounts of very small doses are released throughout the night (eg. 20 mg/hour), coinciding with the period during the day when lung function deteriorates the most due to a decreased cough reflex, a lower tidal breathing and/or a sleep position, resulting in poor clearance of secretions.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of flowing a medicament containing powder using controlled volumes of gas to release controlled amounts of said powder, comprising:

opening a sealed capsule containing a dosage of a powder, said dosage of powder including a quantity of medicament suitable for a single therapeutically effective treatment;

providing a volume of a gas initiated according to one or more release conditions;

directing flow of said gas through said capsule; and controlling delivery of said dosage of the powder using said gas;

wherein said controlled delivery is executed by providing said volume of gas in a plurality of bursts including a first burst and at least one subsequent burst, a said at least one subsequent burst including an adjusted volume of gas suitable to release an adjusted portion of said dosage of said powder, wherein a planned amount of powder to deliver is adjusted to provide said adjusted portion of said dosage of said powder prior to providing said subsequent burst and includes an amount of powder smaller than the total amount of said dosage, said plurality of bursts configured to achieve a total delivery of said dosage.

2. The method according to claim 1, wherein said controlling delivery comprises releasing according to breath considerations.

3. The method according to claim 2, wherein said breath considerations comprises an inspiratory flow rate.

4. The method according to claim 2, wherein said breath considerations comprises an inspiratory flow volume.

5. The method according to claim 2, wherein said breath considerations comprises a prolonged expiratory phase.

6. The method according to claim 1, wherein said one or more release conditions comprise an inspiratory flow rate higher than a threshold.

7. The method according to claim 1, wherein said one or more release conditions comprise a delay from the start of an inhalation phase.

8. The method according to claim 7, wherein said delay is less than 1.5 seconds.

9. The method according to claim 1, wherein said one or more release conditions comprise a time or a volume before an inert part.

10. The method according to claim 9, wherein said inert part ranges from 25% to 75% of an inspiratory volume.

11. The method according to claim 1, wherein said controlling delivery comprises releasing according to time considerations.

12. The method according to claim 11, wherein said time considerations comprises a time of day.

13. The method according to claim 1, wherein each said burst is less than 0.2 seconds in length.

14. The method according to claim 13, wherein said gas is compressed before a second said plurality of bursts is delivered.

15. The method according to claim 1, wherein said controlling delivery comprises releasing while said plurality of bursts is provided continuously, wherein said continuously is between 0.5 seconds and 5 seconds in length.

16. The method according to claim 1, wherein said controlling delivery of an amount comprises releasing two or more amounts as part of a release logic.

17. The method according to claim 16, wherein said dosage of a powder comprises one powder source.

18. The method according to claim 16, wherein said two or more amounts are different.

19. The method according to claim 16, wherein said two or more amounts are equal.

20. The method according to claim 16, wherein a first amount is released during a morning and a second amount is released during an afternoon.

21. The method according to claim 16, wherein said two or more amounts are dynamically adjusted according to a feedback.

22. The method according to claim 21, wherein said dynamically adjusted comprises dynamically adjusting in real time.

23. The method according to claim 21, wherein said dynamically adjusted comprises dynamically adjusting per breath.

24. The method according to claim 1, wherein said one or more release conditions comprise an external reference.

25. The method according to claim 1, wherein said providing a volume of gas comprises providing by dynamically adjusting said volume.

26. The method according to claim 1, wherein said providing a volume of gas comprises providing by dynamically adjusting a pressure of said gas.

27. The method according to claim 1, wherein said controlling delivery comprises inhaling as part of a medical therapy.

28. The method according to claim 1, wherein said controlling delivery comprises blowing into a body cavity.

29. The method according to claim 1, wherein said flow of said gas deagglomerates said powder.

30. The method according to claim 1, wherein said flow of said gas aerosolizes said powder.

31. The method according to claim 1, further comprising:
providing a first amount of said powder in a capsule;
forming one or more apertures in said capsule; and
controlling the release of a second amount of said powder from said capsule, wherein said second amount is less than said first amount.

32. The method according to claim 31, wherein said second amount is released from the same capsule as said first amount.

33. The method according to claim 1, further comprising:
releasing a therapeutically effective first amount of said powder during a breathing cycle; and
releasing a therapeutically effective second amount of said powder during said breathing cycle, wherein said first and second amounts are separated by a period of time.

34. The method according to claim 33, wherein said releasing comprises releasing by flowing a gas through said powder.

35. The method of claim 1, wherein said single therapeutic treatment comprises a treatment administered from the capsule wherein a plurality of adjusted portions of said powder is delivered over a plurality of respiration cycles wherein said one or more release conditions are met.

36. The method of claim 1, wherein said single therapeutic treatment comprises a treatment administered from the capsule wherein a plurality of adjusted portions of said powder is delivered over the course of several hours of a day wherein said one or more release conditions are met.

37. The method of claim 1, wherein a plurality of adjusted portions of said powder is delivered from the capsule within a single respiratory cycle.

38. The method of claim 1, wherein a predetermined amount of said powder remains in the capsule after the completed release of said predetermined therapeutically effective amount.

39. The method according to claim 1, wherein presetting of a volume of gas is provided prior to said opening of said sealed capsule.

40. The method according to claim 1, wherein each said adjusted volume of gas is proportional to a corresponding said adjusted portion of said powder.

41. The method according to claim 1, wherein at least one of said controlled volumes of gas is preselected.

42. The method according to claim 1, wherein a total of all said adjusted portions of said dosage of powder is equal to a said dosage of powder.

43. An apparatus for flowing a medicament containing dry powder using controlled volumes of gas to release controlled amounts of said powder, comprising:
a source of a gas;
a staging chamber configured to:
receive and open a sealed capsule containing a dosage of a dry powder, said dosage of dry powder including a quantity of medicament suitable for a single therapeutically effective treatment, and
direct a plurality of bursts of said gas through said capsule, wherein said plurality of bursts includes a first burst and at least one subsequent burst; and
a controller, configured to control said plurality of bursts to release said medicament into an inspiratory flow, wherein a said at least one subsequent burst has an adjusted volume of gas suitable to release an adjusted portion of said dosage of said powder, wherein a planned amount of powder to deliver is adjusted to provide said adjusted portion of said dosage of said powder prior to providing said subsequent burst and includes an amount of powder smaller than the total amount of said dosage, to achieve a total delivery of said dosage.

44. The apparatus according to claim 43, wherein said gas is a volume of a gas.

45. The apparatus according to claim 43, further comprising a compressor.

46. The apparatus according to claim 45, further comprising a piston to compress said gas in a cylinder.

47. The apparatus according to claim 43, further comprising a tank to store said gas.

48. The apparatus according to claim 43, further comprising a handpump to compress said gas.

49. The apparatus according to claim 43, further comprising at least one said capsule containing said powder positioned in said staging chamber.

50. The apparatus according to claim 49, further comprising a magazine of said capsules comprising said powder.

51. The apparatus according to claim 49, further comprising a piercing mechanism to pierce one or more holes in said capsule, thereby opening said sealed capsule.

52. The apparatus according to claim 43, wherein said controller is configured to dynamically control the release of said powder according to a feedback.

53. The apparatus according to claim 43, further comprising a facemask, said facemask in fluid communication with said staging chamber.

54. The apparatus according to claim 43, further comprising a safety mechanism to restrict access to said powder.

55. The apparatus according to claim 54, wherein said safety mechanism prevents access to said powder.

56. The apparatus according to claim 54, wherein said safety mechanism disposes of said powder.

57. The apparatus according to claim 43, further comprising two or more separately stored types of a dry powder.

58. The apparatus according to claim 43, wherein said apparatus is self powered.

59. The apparatus according to claim 43, comprising a flow sensor configured to sense an inspiratory flow rate, and wherein said controller is configured to release said plurality of bursts according to a parameter of said inspiratory flow rate.

60. The apparatus according to claim 43 wherein said released therapeutically effective portion of said powder is smaller than the total amount of said dry powder in a capsule.

61. The apparatus according to claim 43 wherein said releasing comprises releasing said dry powder over a plurality of inspiratory breaths.

62. The apparatus according to claim 43, further comprising a memory having a treatment protocol comprising an association between said controlled volumes of gas and said controlled amounts of said powder.

\* \* \* \* \*